(12) United States Patent
Tsuruoka et al.

(10) Patent No.: US 9,995,740 B2
(45) Date of Patent: Jun. 12, 2018

(54) METHOD OF DETERMINING TEMPERATURE AND METHOD OF DETECTING A TARGET PEPTIDE

(71) Applicant: SYSMEX CORPORATION, Kobe-shi, Hyogo (JP)

(72) Inventors: Rena Tsuruoka, Kobe (JP); Yukiko Miura, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days. days.

(21) Appl. No.: 15/079,139

(22) Filed: Mar. 24, 2016

(65) Prior Publication Data
US 2016/0290999 A1 Oct. 6, 2016

(30) Foreign Application Priority Data

Mar. 31, 2015 (JP) ................. 2015-070865

(51) Int. Cl.
| | | |
|---|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| G01N 33/542 | (2006.01) |
| G01N 1/44 | (2006.01) |
| G01N 21/64 | (2006.01) |
| G01N 21/76 | (2006.01) |

(52) U.S. Cl.
CPC ............. *G01N 33/542* (2013.01); *G01N 1/44* (2013.01); *G01N 21/6428* (2013.01); *G01N 21/763* (2013.01); *G01N 2021/6417* (2013.01); *G01N 2021/6432* (2013.01); *G01N 2021/6441* (2013.01); *G01N 2333/76* (2013.01)

(58) Field of Classification Search
None
See application file for complete search history.

(56) References Cited

U.S. PATENT DOCUMENTS

| | | |
|---|---|---|
| 5,981,200 A | 11/1999 | Tsien et al. |
| 2012/0027740 A1 | 2/2012 | Philippart |
| 2012/0277407 A1 | 11/2012 | Yamamoto et al. |
| 2014/0362888 A1 | 12/2014 | Hansen |

OTHER PUBLICATIONS

"Novabiochem", Merck Biosciences, innovations Jan. 2005, pp. 1-4.
Chi-Yue Wu, et al., "Specific Peptide-Bond Cleavage by Microwave Irradiation in Weak Acid Solution", Journal of Protein Chemistry, 1992, pp. 45-50, vol. 11, No. I.
Nilana M.T. Barros et al., "Neprilysin carboxydipeptidase specificity studies and improvement in its detection with fluorescence energy transfer peptides", Biol. Chem., Apr. 2007, vol. 388, pp. 447-455 (total 10 pages).

*Primary Examiner* — Hasan S Ahmed
*Assistant Examiner* — Kaipeen E Yang
(74) *Attorney, Agent, or Firm* — Sughrue Mion, PLLC

(57) ABSTRACT

Disclosed is a method of determining whether a temperature of a sample has reached a predetermined temperature. The method comprises the steps of: mixing an albumin-containing sample with a peptide reagent comprising a peptide for temperature determination; heating the mixture; detecting an optical change of the mixture; and determining whether the temperature of the mixture has reached the predetermined temperature based on the detection result of the optical change. In the method, a dissociation constant ($K_d$) of binding of the peptide for temperature determination to albumin is 500 μM or more, and the peptide for temperature determination comprises a first labeling substance and a second labeling substance.

8 Claims, 19 Drawing Sheets

SEQUENCE LISTING

```
<160> NUMBER OF SEQ ID NOS: 32

<210> SEQ ID NO 1
<211> LENGTH: 40
<212> TYPE: PRT
<213> ORGANISM: Artificial Sequence
<220> FEATURE:
<223> OTHER INFORMATION: Synthetic sequence of beta amyloid(1-40)

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Artificial Sequence
<220> FEATURE:
<223> OTHER INFORMATION: Synthetic sequence of beta amyloid(1-42)

<400> SEQUENCE: 2

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 3
<211> LENGTH: 18
<212> TYPE: PRT
<213> ORGANISM: Artificial Sequence
<220> FEATURE:
<223> OTHER INFORMATION: Synthetic sequence of RSA21

<400> SEQUENCE: 3

Arg Leu Ile Glu Asp Ile Cys Leu Pro Arg Trp Gly Cys Leu Trp Glu
1               5                   10                  15

Asp Asp

<210> SEQ ID NO 4
<211> LENGTH: 29
<212> TYPE: PRT
<213> ORGANISM: Artificial Sequence
<220> FEATURE:
<223> OTHER INFORMATION: Synthetic sequence of Glucagon (1-29)

<400> SEQUENCE: 4

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 5
<211> LENGTH: 5
<212> TYPE: PRT
<213> ORGANISM: Artificial Sequence
<220> FEATURE:
<223> OTHER INFORMATION: Synthetic sequence of ACTH (7-11)

<400> SEQUENCE: 5

Phe Arg Trp Gly Lys
1               5

<210> SEQ ID NO 6
<211> LENGTH: 10
<212> TYPE: PRT
<213> ORGANISM: Artificial Sequence
<220> FEATURE:
<223> OTHER INFORMATION: Synthetic sequence of (Lys)10

<400> SEQUENCE: 6

Lys Lys Lys Lys Lys Lys Lys Lys Lys Lys
1               5                   10

<210> SEQ ID NO 7
<211> LENGTH: 19
<212> TYPE: PRT
<213> ORGANISM: Artificial Sequence
<220> FEATURE:
<223> OTHER INFORMATION: Synthetic sequence of Kininorgen

<400> SEQUENCE: 7

His Asn Leu Gly His Gly His Lys His Glu Arg Asp Gln Gly His Gly
1               5                   10                  15

His Gln Arg
```

<210> SEQ ID NO 8
<211> LENGTH: 16
<212> TYPE: PRT
<213> ORGANISM: Artificial Sequence
<220> FEATURE:
<223> OTHER INFORMATION: Synthetic sequence of C3f(16aa)

<400> SEQUENCE: 8

Ser Ser Lys Ile Thr His Arg Ile His Trp Glu Ser Ala Ser Leu Leu
1               5                   10                  15

<210> SEQ ID NO 9
<211> LENGTH: 18
<212> TYPE: PRT
<213> ORGANISM: Artificial Sequence
<220> FEATURE:
<223> OTHER INFORMATION: Synthetic sequence of SA21

<400> SEQUENCE: 9

Asp Asp Glu Trp Leu Cys Gly Trp Arg Pro Leu Cys Ile Asp Glu Ile
1               5                   10                  15

Leu Arg

<210> SEQ ID NO 10
<211> LENGTH: 15
<212> TYPE: PRT
<213> ORGANISM: Artificial Sequence
<220> FEATURE:
<223> OTHER INFORMATION: Synthetic sequence of ACTH (2-16)

<400> SEQUENCE: 10

Tyr Ser Met Glu His Phe Arg Trp Gly Lys Pro Val Gly Lys Lys
1               5                   10                  15

<210> SEQ ID NO 11
<211> LENGTH: 3
<212> TYPE: PRT
<213> ORGANISM: Artificial Sequence
<220> FEATURE:
<223> OTHER INFORMATION: Synthetic sequence of (His)3

<400> SEQUENCE: 11

His His His
1

<210> SEQ ID NO 12
<211> LENGTH: 25
<212> TYPE: PRT
<213> ORGANISM: Artificial Sequence
<220> FEATURE:
<223> OTHER INFORMATION: Synthetic sequence of Fibrinogen alpha

<400> SEQUENCE: 12

Asp Glu Ala Gly Ser Glu Ala Asp His Glu Gly Thr His Ser Thr Lys
1               5                   10                  15

Arg Gly His Ala Lys Ser Arg Pro Val
            20                  25

<210> SEQ ID NO 13
<211> LENGTH: 12
<212> TYPE: PRT
<213> ORGANISM: Artificial Sequence
<220> FEATURE:
<223> OTHER INFORMATION: Synthetic sequence of lqp

<400> SEQUENCE: 13

Gly Lys Tyr Phe Asn Ala Ala Glu Tyr His Ala Gln
1               5                   10

<210> SEQ ID NO 14
<211> LENGTH: 24
<212> TYPE: PRT
<213> ORGANISM: Artificial Sequence
<220> FEATURE:
<223> OTHER INFORMATION: Synthetic sequence of ACTH (1-24)

<400> SEQUENCE: 14

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 15
<211> LENGTH: 25
<212> TYPE: PRT
<213> ORGANISM: Artificial Sequence
<220> FEATURE:
<223> OTHER INFORMATION: Synthetic sequence of Factor XIII

<400> SEQUENCE: 15

Ala Val Pro Pro Asn Asn Ser Asn Ala Ala Glu Asp Asp Leu Pro Thr
1               5                   10                  15

Val Glu Leu Gln Gly Val Val Pro Arg
            20                  25

<210> SEQ ID NO 16
<211> LENGTH: 39
<212> TYPE: PRT
<213> ORGANISM: Artificial Sequence
<220> FEATURE:
<223> OTHER INFORMATION: Synthetic sequence of ACTH (1-39)

<400> SEQUENCE: 16

Ser Tyr Ser Met Glu His Phe Arg Trp Gly Lys Pro Val Gly Lys Lys
1               5                   10                  15

Arg Arg Pro Val Lys Val Tyr Pro Asn Ala Gly Glu Asn Glu Ser Ala
            20                  25                  30

Glu Ala Phe Pro Leu Glu Phe
        35

<210> SEQ ID NO 17
<211> LENGTH: 41
<212> TYPE: PRT
<213> ORGANISM: Artificial Sequence
<220> FEATURE:
<223> OTHER INFORMATION: Synthetic sequence of ACTH (1-41)

<400> SEQUENCE: 17

Gly Pro Ser Tyr Ser Met Glu His Phe Arg Trp Gly Lys Pro Val Gly
1               5                   10                  15

Lys Lys Arg Arg Pro Val Lys Val Tyr Pro Asn Gly Ala Glu Asp Glu
            20                  25                  30

Ser Ala Glu Ala Phe Pro Leu Glu Phe
        35                  40

<210> SEQ ID NO 18
<211> LENGTH: 10
<212> TYPE: PRT
<213> ORGANISM: Artificial Sequence
<220> FEATURE:

<223> OTHER INFORMATION: Synthetic sequence of (Glu)10

<400> SEQUENCE: 18

Glu Glu Glu Glu Glu Glu Glu Glu Glu Glu
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Synthetic sequence of Dynorphin A

<400> SEQUENCE: 19

Tyr Gly Gly Phe Leu Arg Arg Ile Arg Pro Lys Leu Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic sequence of (Gly)10

<400> SEQUENCE: 20

Gly Gly Gly Gly Gly Gly Gly Gly Gly Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic sequence of (Arg)10

<400> SEQUENCE: 21

Arg Arg Arg Arg Arg Arg Arg Arg Arg Arg
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Synthetic sequence of Cp6

<400> SEQUENCE: 22

Asp Ile Gly Glu Glu Phe Asn Gln
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic sequence of C4a

<400> SEQUENCE: 23

Asn Gly Phe Lys Ser His Ala Leu Gln Leu Asn Asn Arg Gln Ile
1               5                   10                  15

<210> SEQ ID NO 24
<211> LENGTH: 32
<212> TYPE: PRT
<213> ORGANISM: Artificial Sequence
<220> FEATURE:
<223> OTHER INFORMATION: Synthetic sequence of BNP

```
<400> SEQUENCE: 24

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

<210> SEQ ID NO 25
<211> LENGTH: 9
<212> TYPE: PRT
<213> ORGANISM: Artificial Sequence
<220> FEATURE:
<223> OTHER INFORMATION: Synthetic sequence of Bradykinin

<400> SEQUENCE: 25

Arg Pro Pro Gly Phe Ser Pro Phe Arg
1               5

<210> SEQ ID NO 26
<211> LENGTH: 13
<212> TYPE: PRT
<213> ORGANISM: Artificial Sequence
<220> FEATURE:
<223> OTHER INFORMATION: Synthetic sequence of HSA237-249

<400> SEQUENCE: 26

Ala Trp Ala Val Ala Arg Leu Ser Gln Arg Phe Pro Lys
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Synthetic sequence of C3f (8aa)

<400> SEQUENCE: 27

Ser Ser Lys Ile Thr His Arg Ile
1               5

<210> SEQ ID NO 28
<211> LENGTH: 21
<212> TYPE: PRT
<213> ORGANISM: Artificial Sequence
<220> FEATURE:
<223> OTHER INFORMATION: Synthetic sequence of ITIH4

<400> SEQUENCE: 28

Asn Val His Ser Ala Gly Ala Ala Gly Ser Arg Met Asn Phe Arg Pro
1               5                   10                  15

Gly Val Leu Ser Ser
            20

<210> SEQ ID NO 29
<211> LENGTH: 17
<212> TYPE: PRT
<213> ORGANISM: Artificial Sequence
<220> FEATURE:
<223> OTHER INFORMATION: Synthetic sequence of HSA397-413

<400> SEQUENCE: 29

Val Phe Asp Glu Phe Lys Pro Leu Val Glu Glu Pro Gln Asn Leu Ile
1               5                   10                  15

Lys
```

```
<210> SEQ ID NO 30
<211> LENGTH: 11
<212> TYPE: PRT
<213> ORGANISM: Artificial Sequence
<220> FEATURE:
<223> OTHER INFORMATION: Synthetic sequence of HSA599-609

<400> SEQUENCE: 30

Leu Val Ala Ala Ser Gln Ala Ala Leu Gly Leu
1               5                   10

<210> SEQ ID NO 31
<211> LENGTH: 31
<212> TYPE: PRT
<213> ORGANISM: Artificial Sequence
<220> FEATURE:
<223> OTHER INFORMATION: Synthetic sequence of C-peptide

<400> SEQUENCE: 31

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 32
<211> LENGTH: 10
<212> TYPE: PRT
<213> ORGANISM: Artificial Sequence
<220> FEATURE:
<223> OTHER INFORMATION: Synthetic sequence of Colistin
<220> FEATURE:
<221> NAME/KEY: MOD_RES
<222> LOCATION: (1)..(1)
<223> OTHER INFORMATION: 6-methyl-1-oxooctyl-Dbu or 6-methyl-1-
      oxoheptyl--Dbu
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (4)..(4)
<223> OTHER INFORMATION: Dbu
<220> FEATURE:
<221> NAME/KEY: MISC_FEATURE
<222> LOCATION: (4)..(4)
<223> OTHER INFORMATION: Xaa at position 4 and Thr ar position 10
      unitedly form a ring
<220> FEATURE:
<221> NAME/KEY: MOD_RES
<222> LOCATION: (5)..(5)
<223> OTHER INFORMATION: Dbu
<220> FEATURE:
<221> NAME/KEY: MISC_FEATURE
<222> LOCATION: (6)..(6)
<223> OTHER INFORMATION: D-leucine
<220> FEATURE:
<221> NAME/KEY: MOD_RES
<222> LOCATION: (8)..(8)
<223> OTHER INFORMATION: Dbu
<220> FEATURE:
<221> NAME/KEY: MOD_RES
<222> LOCATION: (9)..(9)
<223> OTHER INFORMATION: Dbu
<220> FEATURE:
<221> NAME/KEY: NON_TER
<222> LOCATION: (10)..(10)
<220> FEATURE:
<221> NAME/KEY: MISC_FEATURE
<222> LOCATION: (10)..(10)
<223> OTHER INFORMATION: Xaa at a position 4 and Thr at a position 10
      unitedly form a ring
```

-continued

```
<400> SEQUENCE: 32

Xaa Thr Xaa Xaa Xaa Leu Leu Xaa Xaa Thr
1               5                   10
```

US 9,995,740 B2

METHOD OF DETERMINING TEMPERATURE AND METHOD OF DETECTING A TARGET PEPTIDE

CROSS REFERENCE TO RELATED APPLICATIONS

This application claims priority from prior Japanese Patent Application No. 2015-070865, filed on Mar. 31, 2015, entitled "METHOD OF DETERMINING TEMPERATURE, METHOD OF DETECTING A TARGET PEPTIDE, AND REAGENT FOR DETERMINING TEMPERATURE", the entire contents of which are incorporated herein by reference.

TECHNICAL FIELD

The present invention relates to a method of determining temperature and a method of detecting a target peptide.

BACKGROUND

A target peptide included in an albumin-containing sample, such as a disease marker, forms a complex with albumin in some cases. As a method of liberating the peptide from albumin, for example, the method described in US 2012/027740 is suggested.

In the method described in US 2012/027740, a sample containing a complex of a peptide and albumin is heated at a predetermined temperature to allow albumin to self-associate, thereby liberating the peptide from albumin.

SUMMARY OF THE INVENTION

The scope of the present invention is defined solely by the appended claims, and is not affected to any degree by the statements within this summary.

The present invention provides a method of determining temperature and a reagent for determining temperature that can simply determine whether the temperature of a sample during heating treatment has reached a predetermined temperature, and a method of detecting a target peptide using the method and the reagent.

A first aspect of the present invention is a method of determining whether a temperature of a sample has reached a predetermined temperature. The method comprises the steps of: mixing an albumin-containing sample with a peptide reagent comprising a peptide for temperature determination; heating the mixture; detecting an optical change of the mixture; and determining whether the temperature of the mixture has reached the predetermined temperature based on the detection result of the optical change. In the method, a dissociation constant ($K_d$) of binding of the peptide for temperature determination to albumin is 500 µM or more, and the peptide for temperature determination comprises a first labeling substance and a second labeling substance.

A second aspect of the present invention is a method of detecting a target peptide. The method comprises the steps of: mixing a sample with a peptide reagent, the sample comprising a target peptide and albumin, and the peptide reagent comprising a peptide for temperature determination; heating the mixture; detecting an optical change of the mixture before and after heating; determining whether the temperature of the mixture has reached a predetermined temperature based on the detection result of the optical change, and collecting a supernatant of the mixture and detecting the target peptide in the supernatant when it is determined that the temperature of the mixture has reached the predetermined temperature in the determining step. In the method, a dissociation constant ($K_d$) of binding of the peptide for temperature determination to albumin is 500 µM or more, and the peptide for temperature determination comprises a first labeling substance and a second labeling substance.

A third aspect of the present invention is a method of detecting a target peptide. The method comprises the steps of: mixing a sample, a first peptide reagent and a second peptide reagent, wherein the sample comprises a target peptide and albumin, the first peptide reagent comprises a peptide for temperature determination and the second peptide reagent comprises a peptide for phase partition determination comprising a fluorescent substance; heating the mixture; detecting an optical change of the mixture before and after heating; detecting an fluorescence of the fluorescent substance of the peptide for phase partition determination; determining whether the temperature of the mixture has reached a predetermined temperature based on the detection result of the optical change, determining whether a precipitate of a self-aggregate of albumin is formed and the target peptide is present in a supernatant based on the detection of the fluorescence of the fluorescent substance of the peptide for phase partition determination; collecting the supernatant of the mixture and detecting the target peptide in the supernatant when it is determined that the temperature of the mixture has reached the predetermined temperature and the precipitate is formed and the target peptide is present in the supernatant in the determining step. In the method, a dissociation constant ($K_d$) of binding of the peptide for temperature determination to albumin is 500 µM or more, a dissociation constant ($K_d$) of binding of the peptide for phase partition determination to albumin is less than 500 µM, and the peptide for temperature determination comprises a first labeling substance and a second labeling substance.

DETAILED DESCRIPTION OF THE PREFERRED EMBODIMENTS

1. Method of Determining a Temperature

Figure 1:
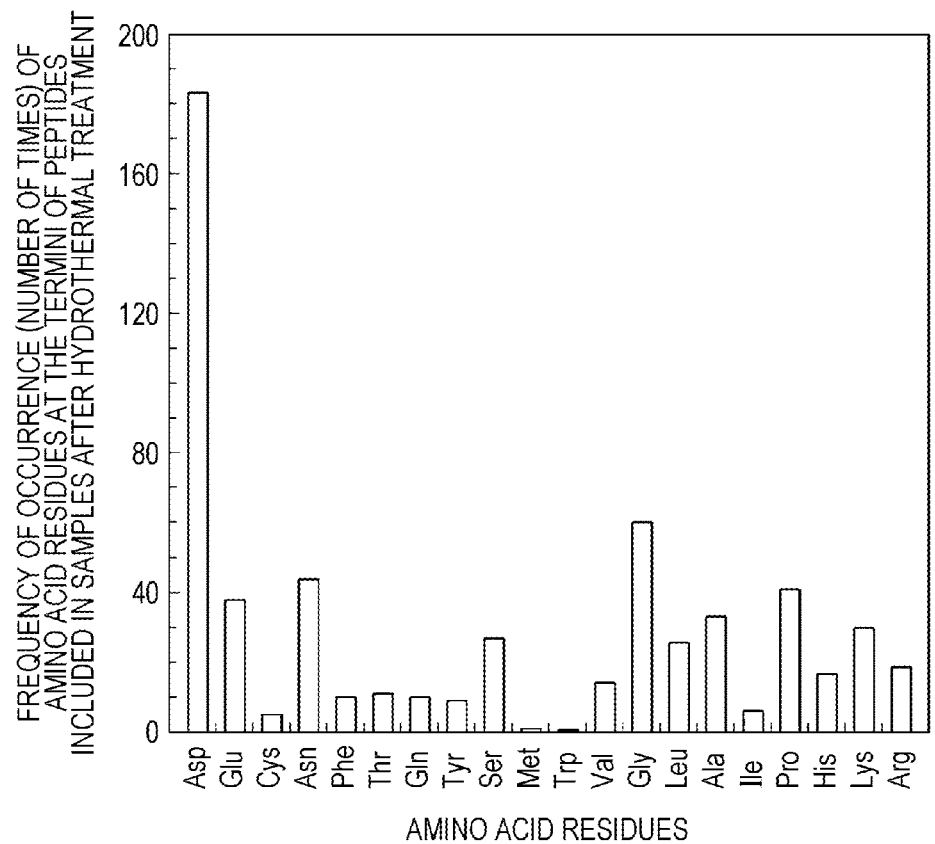
FIG. 1 is a graph showing the analyzed results of the frequency of occurrence of amino acid residues at the termini of the peptides included in a sample after hydrothermal treatment in Reference example 1.

The method of determining a temperature according to the embodiment is a method of determining a temperature that determines whether the temperature of a sample has reached a predetermined temperature. This method comprises the steps of: mixing an albumin-containing sample with a peptide reagent comprising a peptide for temperature determination to give a mixture (hereinafter, also referred to as a "mixing step"); heating the mixture (hereinafter, also referred to as a "heating step"); detecting an optical change of the mixture (hereinafter, also referred to as an "optical change detecting step"); and determining whether the temperature of the mixture has reached the predetermined temperature based on the detection result of the optical change (hereinafter, also referred to as a "determining step"), wherein a dissociation constant ($K_d$) of binding of the peptide for temperature determination to albumin is 500 μM or more, and the peptide for temperature determination includes a first labeling substance and a second labeling substance.

In the embodiment, an albumin-containing sample is used. Examples of the sample include biological samples. Examples of the biological samples include body fluids such as whole blood and lymph fluid; excrements such as urine; and samples obtained by pretreatment of these biological samples, but are not limited thereto. Examples of the samples obtained by pretreatment of these biological samples include plasma and serum.

The predetermined temperature is a temperature that allows albumin to self-associate and causes an optical change based on the cleavage of the peptide for temperature determination. This temperature is preferably 120° C. or more, more preferably 140° C. or more. The upper limit of the predetermined temperature is required to be a temperature that enables detection of optical changes based on the cleavage of the peptide for temperature determination. Usually, the upper limit of the predetermined temperature is preferably 260° C. In the case where the method of determining temperature according to the embodiment is used to detect a target peptide, it is necessary to ensure that the target peptide is not degraded beyond detection by heating at a predetermined temperature. The heating conditions should be conditions where the heat-treated target peptide or a fragment of the target peptide showing the presence of the target peptide can be specifically detected. This temperature is set according to the kind of the target peptide.

The peptide for temperature determination is a peptide whose dissociation constant for albumin is 500 μM or more. Accordingly, the peptide for temperature determination is hardly bound to or associated with albumin in a sample. The peptide for temperature determination includes the linker peptide described below, and the first and second labeling substances. The linker peptide has the first labeling substance and the second labeling substance.

The term "dissociation constant ($K_d$)" used herein means a dissociation constant under the following conditions: normal pressure; 25° C.; a pH of 7.5; and an electrical conductivity (hereinafter also referred to as "conductivity") of 10 mS/cm. A higher dissociation constant of the peptide for temperature determination for albumin means that the peptide for temperature determination has a low affinity for albumin.

The term "linker peptide" used herein means a peptide of 2 to 130 amino acid residues. The linker peptide may be a synthetic or natural peptide. There is no particular limitation as to the isoelectric point of the linker peptide. Examples of the linker peptide include Adrenocorticotropic hormone (ACTH) (1-39) [ACTH (1-39)](SEQ ID NO: 16), ACTH (1-41) (SEQ ID NO: 17), (Glu) 10 (SEQ ID NO: 18), Dynorphin A (SEQ ID NO: 19), (Gly) 10 (SEQ ID NO: 20), (Arg) 10 (SEQ ID NO: 21), Cp6 (SEQ ID NO: 22), C4a (SEQ ID NO: 23), Brain natriuretic peptide (BNP, SEQ ID NO: 24), Bradykinin (SEQ ID NO: 25), HSA 237-249 fragment (SEQ ID NO: 26), C3f (SEQ ID NO: 27), ITIH4 (SEQ ID NO: 28), HSA 397-413 fragment (SEQ ID NO: 29), HSA 599-609 fragment (SEQ ID NO: 30), C-peptide (SEQ ID NO: 31), and colistin (SEQ ID NO: 32), but are not limited thereto. Colistin may be any of colistin A alone, colistin B alone, and a mixture of colistin A and colistin B.

In the linker peptide, there is no particular limitation as to the sites of addition of the first labeling substance and the second labeling substance. The sites of addition are required to be positions where the first labeling substance and the second labeling substance are separated from each other by the cleavage of the linker peptide described below. Preferably, the first labeling substance is bound to the N terminus of the linker peptide and the second labeling substance is bound to the C-terminus thereof such that the first labeling substance is reliably separated from the second labeling substance by the cleavage.

It is preferable that the first labeling substance and the second labeling substance produce a detectable optical change by the cleavage of the peptide for temperature determination. It is easy to detect the optical change. Therefore, the optical change is preferably a change in wavelength of an optical signal due to the peptide for temperature determination. Examples of the change in wavelength of the optical signal include a change in wavelength of light and fluorescence generation, but are not limited thereto. The term "fluorescence generation" used herein means that fluorescence with an intensity of higher than or equal to a predetermined threshold is generated after heat treatment. In the case where fluorescence is not generated before heat treatment or in the case where the fluorescence intensity is less than the threshold, the "fluorescence generation" can be detected as the optical change. In the embodiment, the first labeling substance and the second labeling substance may be appropriately selected from a labeling substance utilizing fluorescent resonance energy transfer (FRET) and a labeling substance utilizing bioluminescence resonance energy transfer (BRET).

FRET is a phenomenon in which energy is directly transferred between two adjacent fluorescent substances by electronic resonance. In FRET, the energy of the excitation light absorbed by the donor is transferred to an acceptor i.e., the fluorescent substance. As a result, fluorescence is emitted from the acceptor. BRET is a phenomenon in which energy used to emit light from a bioluminescent substance is transferred to a fluorescent substance disposed near a luminescent substance and fluorescence is generated.

Examples of the first labeling substance include a fluorescent substance serving as an energy donor and a bioluminescent substance serving as an energy donor, but are not limited thereto. Examples of the second labeling substance include a quencher of fluorescence resulting from the fluorescent substance used as the first labeling substance (a fluorescent substance serving as an acceptor which receives energy from the fluorescent substance serving as a donor) and a fluorescent substance serving as an acceptor which receives energy from the bioluminescent substance used as the first labeling substance, but are not limited thereto.

Examples of the fluorescent substance serving as an energy donor include 5-((2-aminoethyl)amino)naphthalene-1-sulfonic acid, 7-methoxycoumarin-4-acetic acid, fluorescein 5(6) isothiocyanate, 6-carboxyfluorescein, tetrachlorofluorescein, Rhodamine green (trademark), tetramethyl rhodamine, carboxy rhodamine, Cy5 (trademark), Cyanin5 (trademark), ATTO 655 (trademark), STELLATM-488 (trademark), STELLATM-600 (trademark), and fluorescent nanoparticles, but are not limited thereto. The fluorescent substance serving as an energy donor is preferably 5-((2-aminoethyl)amino)naphthalene-1-sulfonic acid and 7-methoxycoumarin-4-acetic acid in view of ease of detection of fluorescence. Examples of the bioluminescent substance serving as an energy donor include photoproteins such as luciferase, but are not limited thereto. Examples of the quencher include 4-[4-(dimethylamino)phenylazo]benzoic acid, 2,4-dinitrophenol, tetramethyl rhodamine, BHQ-1 (trademark), BHQ-2 (trademark), 7-nitrobenzofurazan, and Cy5Q (trademark), but are not limited thereto. The quencher is preferably 4-[4-(dimethylamino)phenylazo]benzoic acid and 2,4-dinitrophenol in view of ease of detection of fluorescence. Examples of the fluorescent substance serving as an acceptor which receives energy from the bioluminescent substance include green fluorescent proteins, but are not limited thereto. A combination of the first labeling substance and the second labeling substance can be appropriately determined.

A distance between the first labeling substance and the second labeling substance on the linker peptide is sufficiently close. In the case of utilizing resonance energy transfer, the distance may be a distance that allows the energy transfer to occur. When the first labeling substance is separated from the second labeling substance by heat treatment, the energy transfer does not occur. This results in an optical change. For example, in the case where a combination of the first labeling substance and the second labeling substance is a combination of a fluorescent substance utilizing FRET and a quencher, the distance between the first labeling substance and the second labeling substance on the linker peptide is required to be a distance that allows the quencher to quench fluorescence resulting from the fluorescent substance. In this case, the upper limit of the distance between the first labeling substance and the second labeling substance is preferably 1111 residues, more preferably 40 residues. In the case of this distance, the quencher can quench the fluorescence.

The cleavage of the peptide for temperature determination is assumed to be due to cleavage of the peptide bond. Aspartic acid, glutamic acid, asparagine, serine, glycine, leucine, alanine, proline, and lysine residues are considered to be easily cleaved at the N-terminal or C-terminal side by heat treatment. Therefore, the peptide for temperature determination preferably includes at least one amino acid residue of the above residues, more preferably includes the aspartic acid residue.

The peptide for temperature determination to be used may be dissolved in an adjuvant such as a buffer.

In the method of determining temperature according to the embodiment the albumin-containing sample is first mixed with the peptide for temperature determination in the mixing step. In the mixing step, the amount of the peptide for temperature determination to a sample can be appropriately determined according to the amount of protein or peptide included in the sample, the kind of the sample or the like.

Next, in the heating step, the mixture obtained in the mixing step is heated. The heating temperature is the same as the predetermined temperature. The heating time is required to be a time sufficient to heat the mixture to the predetermined temperature. Usually, the heating time is, for example, 5 minutes or more.

Examples of a method of heating the mixture include a heating method by microwave irradiation and a heating method by external heat conduction, but are not limited thereto. Examples of a device used to heat the mixture include a hydrothermal reactor and a microwave applicator, but are not limited thereto.

When being heated at the predetermined temperature, albumin molecules associate with one another to form an insoluble precipitate. However, the peptide for temperature determination is hardly bound to albumin in the sample. Thus, the peptide for temperature determination is not entrapped in an insoluble precipitate of albumin when being heated. Accordingly, when the temperature of the mixture reaches the predetermined temperature in the heating step, the peptide for temperature determination is not contained in the insoluble precipitate of albumin, but is present in the liquid component (supernatant). The peptide for temperature determination is considered to be cleaved in such a manner that when the temperature of the mixture reaches the predetermined temperature, the peptide bond is cut. Therefore, it is assumed that the distance between the first labeling substance and the second labeling substance is larger than before the heating step and an optical change is likely to occur.

Then, the optical change of the mixture is detected in the optical change detecting step. The optical state before heating may or may not be detected when detecting the optical change. The optical state before heating is known in advance because it is an optical state of the reagent itself. The optical state after heating is detected and compared with the optical state before heating so that the optical change can be detected.

It is assumed that when the mixture is heated to the predetermined temperature, the peptide for temperature determination is cleaved. Thus, it is assumed that the distance between the first labeling substance and the second labeling substance becomes longer than that before performing the heating step and the optical change occurs. In the case where the first labeling substance and the second labeling substance are, for example, a combination of a fluorescent substance used for FRET and a quencher, the cleavage (cutting of the peptide bond) of the peptide for temperature determination allows the distance between the fluorescent substance of the first labeling substance and the quencher of the second labeling substance to be far enough to cause no FRET. As a result, the quencher cannot quench the fluorescence from the fluorescent substance and fluorescence is generated.

Examples of an optical change detection unit include a spectrophotometer, a fluorophotometer, and a combination of an electrophoretic device and an imaging analyzer, but are not particularly limited thereto. The detection unit can be appropriately selected according to the kind of optical change of a detection target substance.

Then, in the determining step, it is determined whether the temperature of the mixture has reached the predetermined temperature based on the detection result of the optical change obtained in the optical change detecting step.

In the determining step, for example, when the intensity of the detected optical signal is higher than or equal to a predetermined threshold, the temperature of the mixture can be determined to be not lower than the predetermined temperature. On the other hand, when the intensity of the detected optical signal is less than the predetermined threshold, the temperature of the mixture can be determined to be lower than the predetermined temperature. The term "predetermined threshold" used herein means a value that can most accurately classify the intensity of the optical signal before heating and the intensity of the optical signal resulting from the cleavage of the peptide for temperature determination by heating.

When the fluorescence from the labeling substance included in the peptide for temperature determination in the supernatant of the mixture is detected in the optical change detecting step, the determination can be made based on the intensity of the fluorescence of the supernatant in the determining step. When the intensity of the fluorescence of the supernatant is higher than or equal to the predetermined threshold, the temperature of the mixture can be determined to be not lower than the predetermined temperature. On the other hand, when the intensity of the fluorescence of the supernatant is less than the predetermined threshold, the temperature of the mixture can be determined to be lower than the predetermined temperature.

When a container containing a sample needs to be sealed and heated, it is difficult to bring a measurement target substance into contact with a thermometer and measure the temperature thereof. In this case, it is difficult to measure the temperature of the sample outside without a non-contact thermometer such as thermography. The use of the peptide for temperature determination of the embodiment enables the temperature of the sample in the container to be simply determined without the thermometer which is brought into contact with the measurement target substance or the non-contact thermometer. Therefore, the method of determining temperature according to the embodiment is suitable for determining the temperature of the sample when the container containing the sample is sealed and heated.

2. Method of Detecting Target Peptide

The method of detecting a target peptide according to the embodiment (hereinafter, simply referred to as a "detection method") includes the steps of mixing a sample containing a target peptide and albumin with a peptide for temperature determination to give a mixture (mixing step), heating the mixture (heating step), detecting an optical change of the mixture (optical change detecting step), and determining whether the temperature of the mixture has reached a predetermined temperature based on the detection result of the optical change (determining step). The peptide for temperature determination is as described above. When the temperature of the mixture is determined to be not lower than the predetermined temperature in the determining step, a step of collecting a supernatant of the mixture (hereinafter, also referred to as a "collecting step") and a step of detecting the target peptide in the supernatant (hereinafter, also referred to as a "target peptide detecting step") are executed. The mixing step, heating step, optical change detecting step, and determining step in the detection method according to the embodiment are the same as those in the above method of determining temperature.

The target peptide of the detection method according to the embodiment is preferably different from the linker peptide of the peptide for temperature determination.

Examples of the target peptide include peptides such as biomarkers in a biological sample, but are not limited thereto. Examples of the biomarkers include ACTH, BNP, atrial natriuretic polypeptide (ANP), bradykinin, α-endorphin, C3f, ITIH4, C-peptide, β-amyloid, endothelin, adrenomedullin, vasopressin, oxytocin, intact type I procollagen-N-propeptide (Intact PINP), and procollagen III peptide (P-III-P), but are not limited thereto.

When the temperature of the mixture is determined to be not lower than the predetermined temperature in the determining step, the collecting step and the target peptide detecting step are executed. On the other hand, when the temperature of the mixture is determined to be lower than the predetermined temperature in the determining step, the collecting step and the target peptide detecting step are not executed.

In the collecting step, the supernatant of the mixture can be collected by centrifugation, ultrafiltration, decantation or the like.

Examples of the method of detecting a target peptide in the target peptide detecting step include methods using an antibody to the target peptide, such as enzyme-linked immunosorbent assay (ELISA), liquid chromatography mass spectrometry (LC/MS, LC/MS/MS), a method using a reflectometric interference spectroscopy sensor, and reflection intensity measurement, but are not limited thereto.

In the detection method according to the embodiment, in the mixing step, a peptide reagent comprising a peptide for phase partition determination having a fluorescent substance may be further mixed, in addition to the sample and the peptide for temperature determination. The term "phase partition" used herein means partitioning into an insoluble precipitate layer and a solution layer (a supernatant). When the albumin-containing sample is heat-treated, a self-aggregate of albumin is formed, and an insoluble precipitate is produced. The insoluble precipitate contains a protein or peptide binding to albumin. The component not binding to albumin is present in the solution layer. The peptide for temperature determination is not bound to albumin, and thus is present in the solution layer. The peptide for phase partition determination is bound to albumin as described below, and thus is present in the insoluble precipitate layer.

The peptide for phase partition determination is a peptide having a $K_d$ of less than 500 μM when binding to albumin. Therefore, the peptide for phase partition determination is likely to bind to albumin in a sample. Consequently, when the temperature of the mixture reaches the predetermined temperature in the heating step, the peptide for phase partition determination is contained in the insoluble precipitate of albumin. In this case, the use of the peptide for phase partition determination enables the phase separation between the insoluble precipitate of albumin formed by heat treatment and the supernatant fraction to be simply determined. An exemplary fluorescent substance is the same fluorescent substance as that used for the peptide for temperature determination. The fluorescent substance of the peptide for phase partition determination is a different substance from the labeling substance of the peptide for temperature determination from the viewpoint of easy detection of the fluorescence resulting from the fluorescent substance in the peptide for phase partition determination.

When the peptide for phase partition determination is used, in the optical change detecting step, the fluorescence resulting from the fluorescent substance in the peptide for phase partition determination contained in the insoluble precipitate of albumin is detected, in addition to the optical change resulting from the peptide for temperature determination.

When the peptide for phase partition determination is used, a precipitate that generates fluorescence based on the fluorescent label of the peptide for phase partition determination is detected in the mixture. When the intensity of the fluorescence from the precipitate is higher than or equal to a predetermined threshold, it can be determined that the phase partition is appropriately performed.

3. Reagent for Determining Temperature

The reagent for determining temperature according to the embodiment includes the peptide for temperature determination. This reagent may be a reagent prepared from the peptide for temperature determination alone or may be a reagent prepared by dissolving the peptide for temperature determination in a solvent such as water. The reagent for determining temperature may further contain an adjuvant for keeping the peptide stable. Examples of the adjuvant include buffers and preservatives, but are not limited thereto.

The reagent of the embodiment may further include the peptide for phase partition determination. In this case, the reagent is preferably in the form of a reagent kit in which the peptide for temperature determination and the peptide for phase partition determination are placed in different containers.

EXAMPLES

Hereinafter, the amino acid residues may be represented by three letters as shown in Table 1.

TABLE 1

| Amino acid residue | Notation |
| --- | --- |
| Alanine residue | Ala |
| Arginine residue | Arg |
| Asparagine residue | Asn |
| Aspartic acid residue | Asp |
| Cysteine residue | Cys |
| Glutamine residue | Gln |
| Glutamic acid residue | Glu |
| Glycine residue | Gly |
| Histidine residue | His |
| Isoleucine residue | Ile |
| Leucine residue | Leu |
| Lysine residue | Lys |
| Methionine residue | Met |
| Phenylalanine residue | Phe |
| Proline residue | Pro |
| Serine residue | Ser |
| Threonine residue | Thr |
| Tryptophan residue | Trp |
| Tyrosine residue | Tyr |
| Valine residue | Val |

Reference Example 1

With a 0.1 M Tris-HCl buffer (pH 7.0) containing 0.1 M calcium chloride, 150 L of serum from healthy subjects was 10-fold diluted to obtain a serum-containing sample. Then, 1.5 mL of the resulting serum-containing sample was placed in a glass container for hydrothermal treatment. Then, the glass container for hydrothermal treatment containing a diluted solution was put in a microwave synthesis reactor [product name: MultiSYNTH, manufactured by Milestone General K.K.] and the hydrothermal treatment was performed at 160° C. Thereafter, a supernatant was collected from the sample after hydrothermal treatment. The temperature conditions of the hydrothermal treatment at 160° C. were set to the following conditions: increasing from normal temperature (20° C.) to 100° C. over 30 seconds; and increasing from 100° C. to 160° C. over 1 minute.

The resulting supernatant was subjected to ultrafiltration using an ultrafilter [product name: AmiconUltra-0.5 10 kDa, manufactured by Merck Millipore]. The resulting filtrate was desalted using a solid phase extraction column [product name: RP-1, manufactured by GL Sciences Inc.]. The desalted solution was placed in a centrifugal evaporator to dry out. The resulting dried product was dissolved in 100 µL of a mixed solvent of acetonitrile, trifluoroacetic acid (TFA), and water [purified water containing 50% by volume of acetonitrile and 0.1% by volume of TFA]. With 0.1% by volume of a mixed solvent of TFA and purified water, 5 µL of the resulting solution was 50-fold diluted. Then, 5 µL of the resulting diluted solution was placed in a liquid chromatographic device [product name: ADVANCE UPLC SYSTEM, manufactured by Michrom BioResources, Inc.] and a mass spectrometer [product name: Thermo Scientific LTQ Orbitrap XL mass spectrometer, manufactured by Thermo Fisher Scientific Inc.]. Then, the peptides formed by hydrothermal treatment were analyzed by liquid chromatography mass spectrometry (LC-MS/MS). The measurement conditions of liquid chromatography mass spectrometry (LC-MS/MS) as well as the analytical conditions for the measurement results were set to the following conditions.

<Liquid Chromatography Conditions>

Separating column: product name: L-column ODS (0.1× 150 mm), manufactured by Chemicals Evaluation and Research Institute Elution solvent A: mixed solvent of 2% by volume of acetonitrile and 0.1% by volume of formic acid Elution solvent B: mixed solvent of 90% by volume of acetonitrile and 0.1% by volume of formic acid Flow rate: 500 nL/min Concentration gradient: concentration gradient shown in Table 2

TABLE 2

| Elapsed time (min) | Concentration of mixed solvent B in extraction solvent (% by volume) |
|---|---|
| 0 | 5 |
| 15 | 45 |
| 16 | 95 |
| 21 | 95 |
| 22 | 5 |

<Mass Spectrometry Conditions>
Ionization method: Nanoflow-LC ESI
Ionization mode: Positive mode
Capillary voltage: 1.8 kV
Collision energy: 35 eV <Analytical Conditions for Measurement Results>
Analysis software: Mascot Server (in-house database search) provided by Matrix Science, Inc.
Database: NCBInr
Organism species: all entries (all organism species)
Digestive enzyme: none
Modification: oxidation (M)

As a result, 292 kinds of peptides were identified by LC-MS/MS. The frequency of occurrence of amino acid residues at the termini of the peptides included in the sample after hydrothermal treatment is shown in FIG. 1.

Human γ-globulin [manufactured by Wako Pure Chemical Industries, Ltd.] and calcium chloride were dissolved at final concentrations of 20 mg/mL and 0.1 M, respectively, in a 0.1 M Tris-HCl buffer (pH 7.0). Thus, a human γ-globulin-containing sample was obtained. Human serum albumin (hereinafter, also referred to as "HSA") [manufactured by Sigma-Aldrich Co. LLC.] and calcium chloride were dissolved at final concentrations of 40 mg/mL and 0.1 M, respectively, in a 0.1 M Tris-HCl buffer (pH 7.0). Thus, an HSA-containing sample was obtained.

Figure 2:
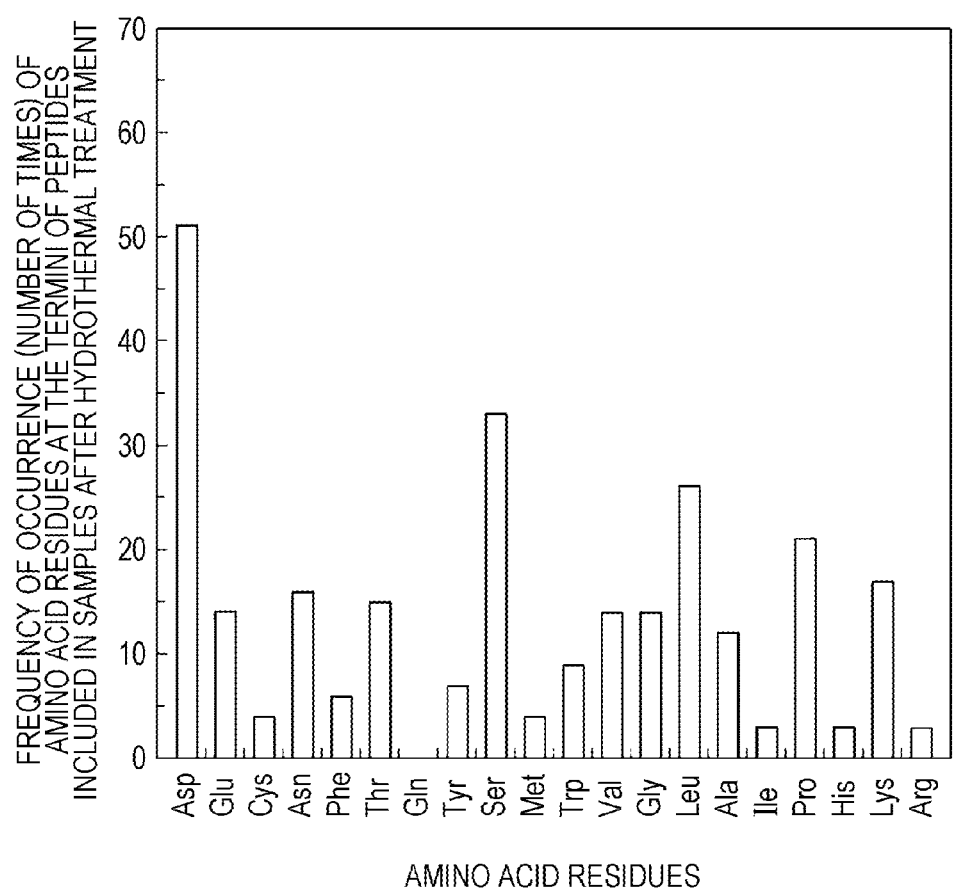
FIG. 2 is a graph showing the analyzed results of the frequency of occurrence of amino acid residues at the termini of the peptides included in a human γ-globulin-containing sample after hydrothermal treatment in Reference example 1.
Figure 3:
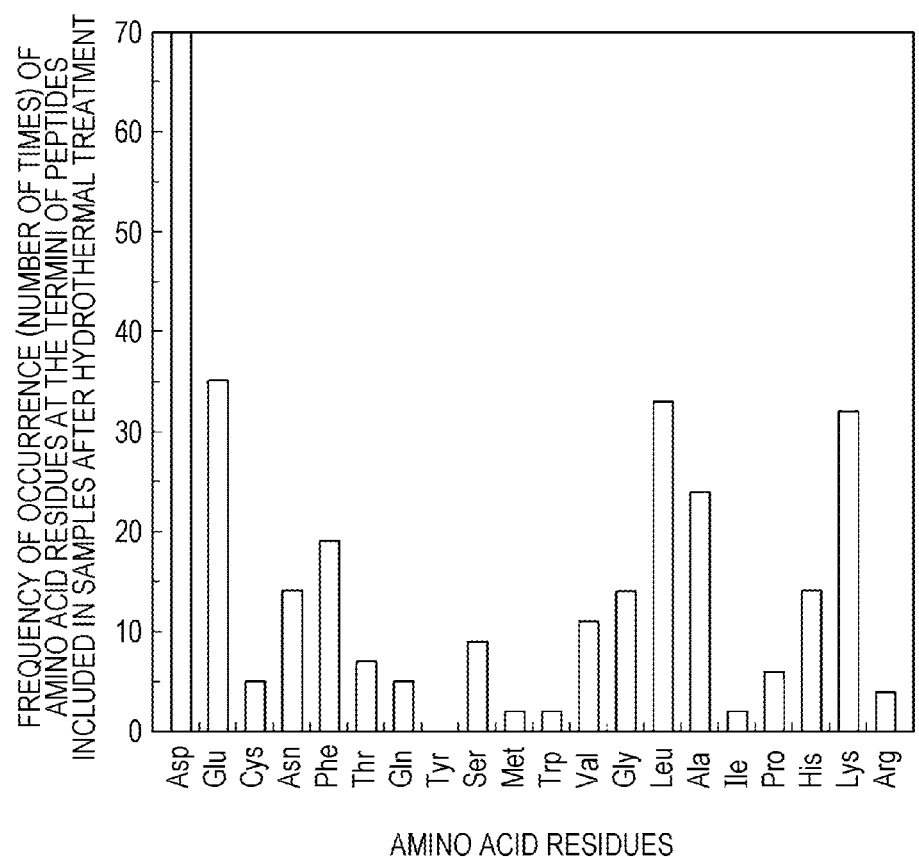
FIG. 3 is a graph showing the analyzed results of the frequency of occurrence of amino acid residues at the termini of the peptides included in a human serum albumin-containing sample after hydrothermal treatment in Reference example 1.
Figure 4:
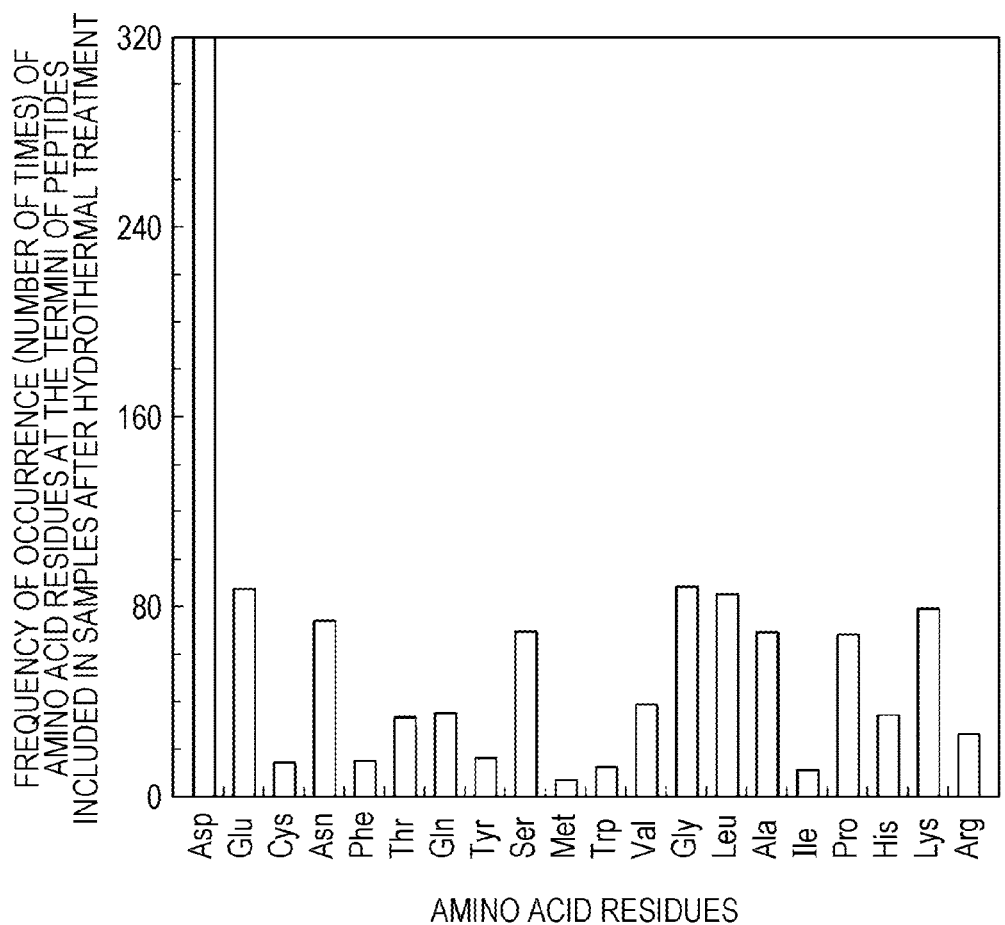
FIG. 4 is a graph showing the analyzed results of the frequency of occurrence of amino acid residues at the termini of the peptides included in a sample prepared by hydrothermal treatment of each of serum, human γ-globulin, and human serum albumin in Reference example 1.

Then, the hydrothermal treatment and LC-MS/MS were performed in the same manner as described above except that the human γ-globulin-containing sample or the HSA-containing sample was used in place of the serum-containing sample. After that, the frequency of occurrence of amino acid residues at the termini of the peptides included in the sample after hydrothermal treatment was determined. FIG. 2 shows the analyzed results of the frequency of occurrence of amino acid residues at the termini of the peptides included in the human γ-globulin-containing sample after hydrothermal treatment. FIG. 3 shows the analyzed results of the frequency of occurrence of amino acid residues at the termini of the peptides included in the human serum albumin-containing sample after hydrothermal treatment. FIG. 4 shows the analyzed results of the frequency of occurrence of amino acid residues at the termini of the peptides formed by hydrothermal treatment of each of serum, human γ-globulin, and human serum albumin.

The results shown in FIGS. 1 to 4 indicate that positions which are easily cleaved by hydrothermal treatment are present in the proteins and peptides in the serum. The positions easily cleaved were preferably the positions of the aspartic acid, glutamic acid, asparagine, serine, glycine, leucine, alanine, proline, and lysine residues, more preferably the position of the aspartic acid residue.

Example 1

HSA (manufactured by Sigma-Aldrich Co. LLC.) was dissolved at a final concentration of 1 µM in phosphate buffered saline to obtain a solution A. The HSA 397-413 fragment (SEQ ID NO: 29) consisting of amino acids at positions 397 to 413 of HSA, the tetramethyl rhodamine (hereinafter, also referred to as "TMR")-labeled HSA 397-413 fragment, and HSA were dissolved at final concentrations of 833 µM, 7 µM, and 1 µM, respectively, in phosphate buffered saline to obtain a solution B. Then, the solutions A and B were mixed at various mixing ratios to prepare various mixtures having a constant concentration of HSA and different concentrations of HSA 397-412 fragment. Each of the resulting mixtures was subjected to measurement with a spectrophotofluorometer [product name: F-7000, manufactured by Hitachi High-Technologies Corporation] and the fluorescence intensity with an excitation wavelength of 540 nm and a fluorescence wavelength of 580 nm (hereinafter, referred to as "fluorescence intensity A") was measured.

The HSA 397-412 fragment and the TMR-labeled HSA 397-412 fragment were dissolved at final concentrations of 833 μM and 7 μM, respectively, in phosphate buffered saline to obtain a solution C. The phosphate buffered saline and the solution C were mixed at various mixing ratios to prepare various mixtures having different concentrations of HSA 397-412 fragment. Each of the resulting mixtures was subjected to measurement with a spectrophotofluorometer [product name: F-7000, manufactured by Hitachi High-Technologies Corporation] and the fluorescence intensity with an excitation wavelength of 540 nm and a fluorescence wavelength of 580 nm (hereinafter, referred to as "fluorescence intensity B") was measured.

The sum of the concentration of the HSA 397-412 fragment and the concentration of the TMR-labeled HSA 397-412 fragment in the mixture (hereinafter, also referred to as "peptide concentration") was calculated.

Equation (I):

$$\text{Difference between fluorescence intensities} = \text{fluorescence intensity } A - \text{fluorescence intensity } B \quad (I)$$

Figure 5:
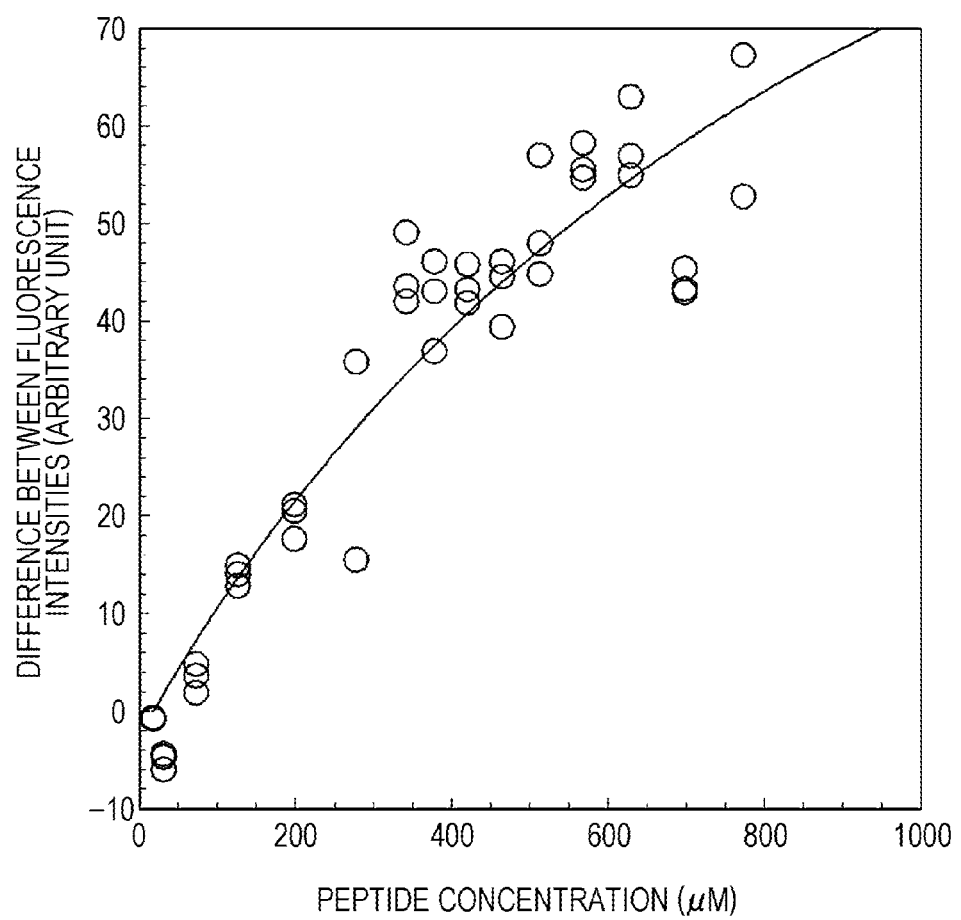
FIG. 5 is a graph showing the analyzed results of the relationship of the peptide concentration with the difference between the fluorescence intensities in Example 1.

A difference between the fluorescence intensities was determined in accordance with the above equation. Data points of the peptide concentration in each of the mixtures and the difference between the fluorescence intensities when using each of the mixtures were plotted on a two-dimensional coordinate, wherein the x-axis shows the peptide concentration and the y-axis shows the difference between the fluorescence intensities. FIG. 5 shows the analyzed results of the relationship of the peptide concentration with the difference between the fluorescence intensities. The approximate curve of the group of the plotted data points, software for graphing and data analysis [product name: KaleidaGraph, manufactured by Hulinks Inc.], and the Hill's equation represented by Equation (II):

$$Y = A \times C^n / C^n + K_d^n \quad (II)$$

(wherein Y represents a fluorescence intensity, A represents a coefficient to compensate the fluorescence intensity, C represents a peptide concentration, $K_d$ represents a dissociation constant, and n represents a Hill coefficient) were used to determine the $K_d$ of the HSA 397-412 fragment for HSA.

As a result, it was found that the $K_d$ of the HSA 397-412 fragment for HSA is 1000 μM or more. Therefore, it was found that the HSA 397-412 fragment has a low affinity for HSA. This result suggests that the HSA 397-412 fragment is hardly bound to HSA.

Example 2

(1) Hydrothermal Treatment

Each of the peptides shown in Table 3 was labeled with TMR.

TABLE 3

| Peptide | Molecular weight | SEQ ID NO: | Number of amino acid residues | pI |
|---|---|---|---|---|
| C3f | 1865 | 8 | 16 | 8.5 |
| ACTH (2-16) | 1850 | 10 | 15 | 10 |
| ACTH (7-11) | 693 | 5 | 5 | 11 |
| Kininogen | 2237 | 7 | 19 | 8.8 |
| (Lys)10 | 1300 | 6 | 10 | 11 |
| RSA21 | 2233 | 3 | 18 | 4.1 |
| SA21 | 2233 | 9 | 18 | 4.1 |
| β-amyloid (1-42) | 4514 | 2 | 42 | 5.3 |
| β-amyloid (1-40) | 4330 | 1 | 40 | 5.3 |
| Glucagon (1-29) | 3483 | 4 | 29 | 6.8 |
| Fibrinogen α | 2660 | 12 | 25 | 6.3 |
| Blood coagulation factor XIII (Factor XIII) | 2603 | 15 | 25 | 3.9 |
| (His)3 | 429 | 11 | 3 | 7 |
| ACTH (1-24) | 2933 | 14 | 24 | 10.6 |
| lqp | 1398 | 13 | 12 | 6.8 |
| ACTH (1-41) | 4695 | 17 | 41 | 8.3 |
| ACTH (1-39) | 4540 | 16 | 39 | 9.3 |
| ITIH4 | 2115 | 28 | 21 | 12 |
| C4a | 1739 | 23 | 15 | 11 |
| Bradykinin | 1060 | 25 | 9 | 12 |
| C3f | 941 | 27 | 8 | 11 |
| (Arg) 10 | 1579 | 21 | 10 | 13 |
| (Glu) 10 | 1309 | 18 | 10 | 3.5 |
| (Gly) 10 | 588 | 20 | 10 | 5.5 |
| Colistin | 1200 | 32 | 10 | — |
| Dynorphin A | 1604 | 19 | 13 | 11.7 |
| Cp6 | 951 | 22 | 8 | 3.6 |
| HSA 237-249 | 1530 | 26 | 13 | 12 |
| HSA 397-413 | 2045 | 29 | 17 | 4.4 |
| HSA 599-609 | 1013 | 30 | 11 | 5.5 |
| C-peptide | 3020 | 31 | 31 | 3.5 |
| BNP | 3466 | 24 | 32 | 11 |

Figure 6:
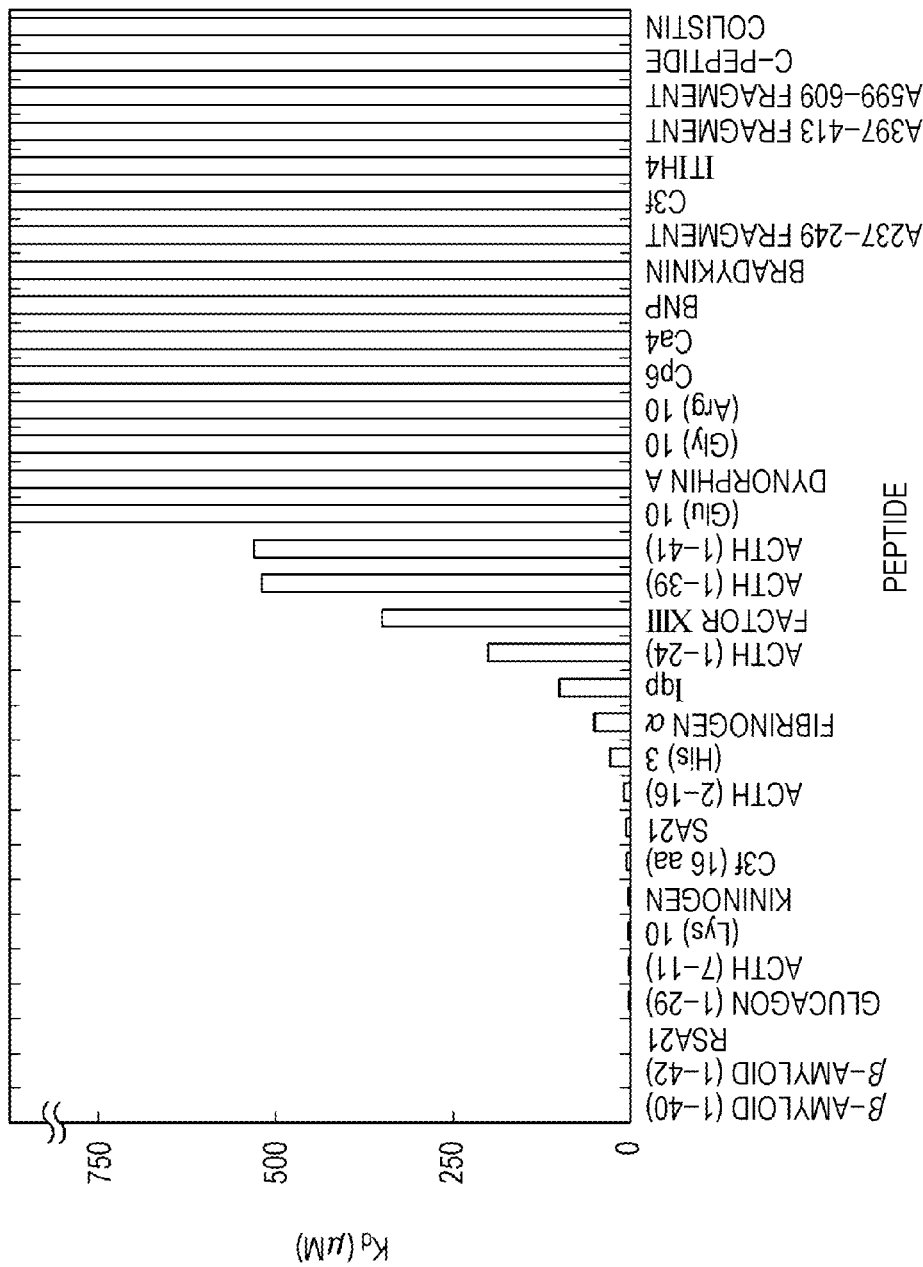
FIG. 6 is a graph showing the analyzed results of the $K_d$ of each of the peptides for HSA in Example 2.

Then, the $K_d$ of each of the peptides shown in Table 3 for HSA was determined in the same manner as in Example 1 except that each of the TMR-labeled peptides was used in place of the HSA 397-412 fragment in Example 1. FIG. 6 shows the $K_d$ of each of the peptides for HSA in Example 2.

The ACTH (1-24) with a $K_d$ of 200 μM for HSA and the ACTH (1-39) with a $K_d$ of 520 μM for HSA were selected from the peptides shown in FIG. 6. The TMR-labeled ACTH (1-24) and HSA were mixed at final concentrations of 5 μM and 470 μM, respectively, with a 0.1 M Tris-HCl solution to obtain a TMR-labeled ACTH (1-24)-containing sample. The TMR-labeled ACTH (1-39) and HSA were mixed at final concentrations of 8 μM and 600 μM, respectively, with a 0.1 M Tris-HCl solution to obtain a TMR-labeled ACTH (1-39)-containing sample.

The hydrothermal treatment was performed in the same manner as in Reference example 1 except that the TMR-labeled ACTH (1-24)-containing sample or the TMR-labeled ACTH (1-39)-containing sample was used in place of the serum-containing sample, the human γ-globulin-containing sample or the HSA-containing sample in Reference example 1. Thereafter, a supernatant was collected from the sample after hydrothermal treatment.

(2) Preparation of Test Sample for SDS-Polyacrylamide Gel Electrophoresis (SDS-PAGE)

First, 10 μL of an additional buffer for SDS-PAGE [product name: 10× Loading Buffer, manufactured by TAKARA BIO INC.] was mixed with 20 μL of an aqueous glycerol solution (60% by volume) to form a buffer for sample. Then, 1.5 μL of the TMR-labeled ACTH (1-24)-containing sample was added to 3 μL of the resulting buffer for sample to obtain a test sample. A test sample was produced in the same manner as described above except that the TMR-labeled ACTH (1-39)-containing sample or a supernatant after hydrothermal treatment of each of the samples was used in place of the TMR-labeled ACTH (1-24)-containing sample in the above process.

(3) SDS-PAGE

Each of the test samples obtained in Example 2 (2) was subjected to SDS-PAGE at a voltage of 200 V using an electrophoretic device [product name: Vertical mini electrophoresis system, manufactured by Invitrogen], an electrophoresis gel [product name: NuPAGE 4-12% Bis-TrisGels, 1.0 mm, 10 wells, manufactured by Invitrogen], and a running buffer [a diluted solution prepared by 20-fold dilution of product name: NuPAGE MES SDS running buffer (20×), manufactured by Invitrogen]. The resulting electrophoresis gel was subjected to analysis with a fluorescence imager [product name: Pharos FX Molecular Imager, manufactured by Bio-Rad Laboratories, Inc.]. The fluorescence image of the electrophoresis gel was captured in High Sample Intensity mode at a wavelength for TAMRA (excitation wavelength: 532 nm).

Figure 7A:
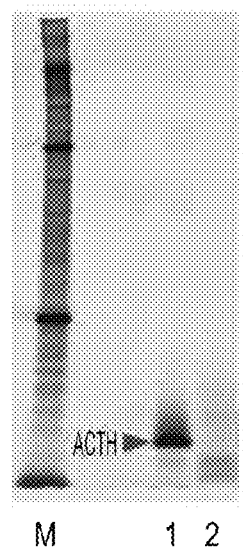
FIG. 7A is a photograph substituted for a drawing showing the electrophoresis gel after SDS-PAGE of the untreated and hydrothermally-treated TMR-labeled ACTH (1-24) in Example 2.
Figure 7B:
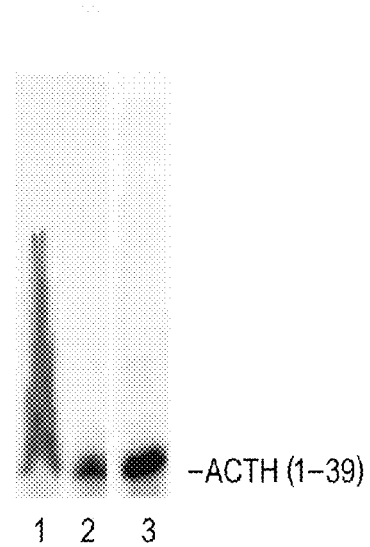
FIG. 7B is a photograph substituted for a drawing showing the electrophoresis gel after SDS-PAGE of the untreated and hydrothermally-treated TMR-labeled ACTH (1-39) in Example 2.

FIGS. 7A and 7B respectively show the results of SDS-PAGE of the untreated and hydrothermally-treated TMR-labeled ACTH (1-24) and the results of SDS-PAGE of the untreated and hydrothermally-treated TMR-labeled ACTH (1-39) in Example 2. In FIG. 7A, Lane M represents the electrophoretic pattern of a molecular weight marker, Lane 1 represents the electrophoretic pattern of the untreated TMR-labeled ACTH (1-24)-containing sample in the presence of HSA, and Lane 2 represents the electrophoretic pattern of the supernatant fraction of the hydrothermally-treated TMR-labeled ACTH (1-24)-containing sample in the presence of HSA. In FIG. 7B, Lane 1 represents the untreated TMR-labeled ACTH (1-39)-containing sample in the presence of HSA, Lane 2 represents the supernatant fraction of the hydrothermally-treated TMR-labeled ACTH (1-39)-containing sample in the presence of HSA, and Lane 3 represents the untreated TMR-labeled ACTH (1-39)-containing sample in the absence of HSA.

The results shown in FIG. 7A indicate that a band derived from the ACTH (1-24) was observed in the electrophoretic pattern of the untreated TMR-labeled ACTH (1-24)-containing sample in the presence of HSA (Lane 1). On the other hand, the band derived from the ACTH (1-24) was not observed in the electrophoretic pattern of the supernatant of the hydrothermally-treated TMR-labeled ACTH (1-24) in the presence of HSA (Lane 2). From this result, the ACTH (1-24) after hydrothermal treatment was expected to be bound to a precipitate of albumin in an insoluble fraction.

On the other hand, the band derived from the ACTH (1-39) was observed in the electrophoretic pattern of the supernatant of the hydrothermally-treated TMR-labeled ACTH (1-39)-containing sample (Lane 2) in the presence of HSA. This result indicates that when the heating temperature reaches the predetermined temperature by heating the ACTH (1-39)-containing sample, the ACTH (1-39) is not bound to the precipitate of albumin in an insoluble fraction, and is present in the supernatant fraction.

Figure 8:
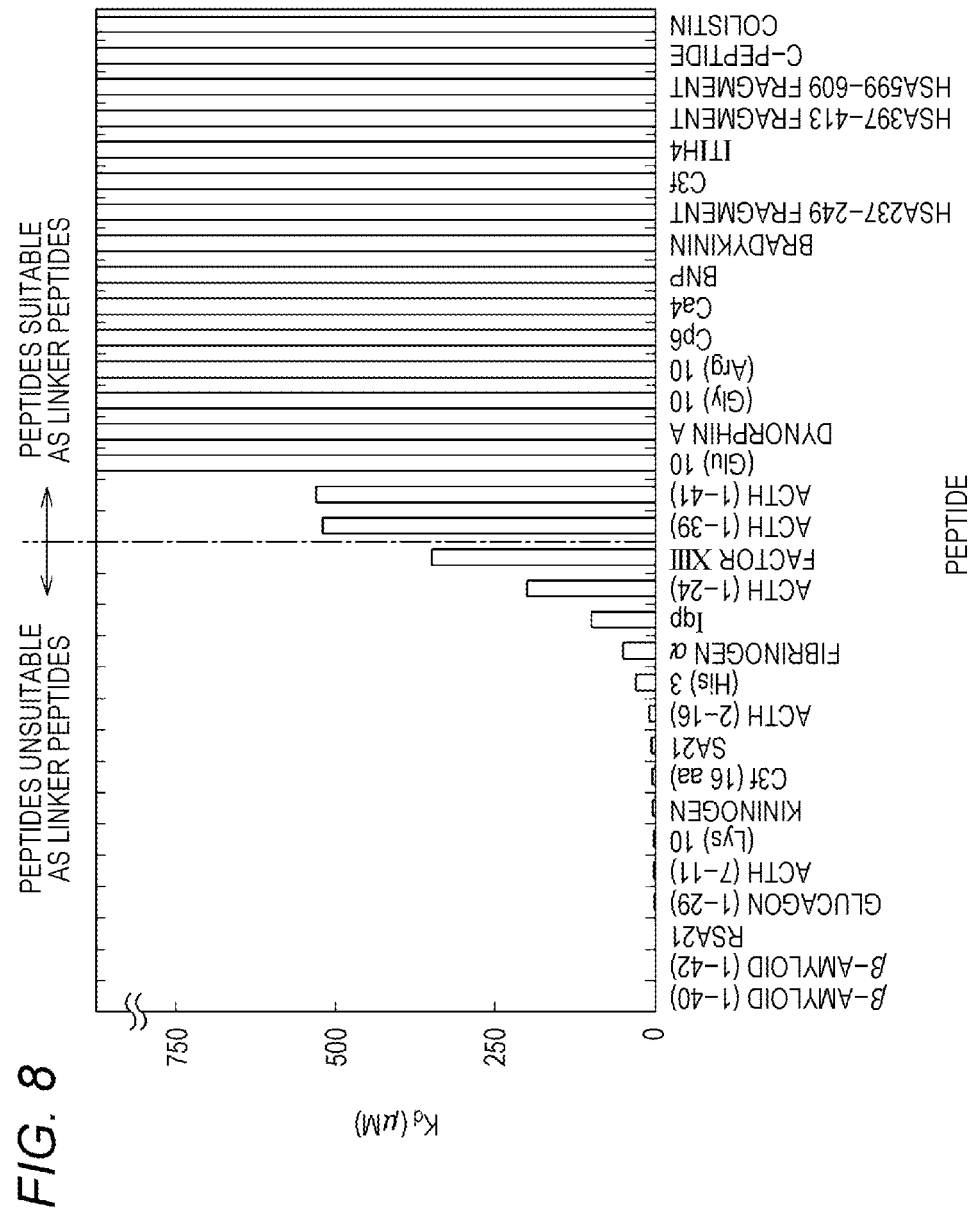
FIG. 8 is a graph showing the results of the peptides in FIG. 6 classified into peptides suitable and unsuitable as linker peptides in Example 2.

These results suggest that when the heating temperature reaches the predetermined temperature by heating in the presence of albumin, the ACTH (1-39) is easily detected in the supernatant fraction. Therefore, it is suggested that the ACTH (1-39) is suitable as a linker portion of the peptide for temperature determination to determine whether the temperature of an albumin-containing sample is the predetermined temperature. These results suggest that the peptide with a $K_d$ of 500 μM or more for albumin is suitable as a linker peptide of the peptide for temperature determination to determine whether the temperature of an albumin-containing sample is the predetermined temperature. FIG. 8 shows the results of the peptides in FIG. 6 classified into peptides suitable and unsuitable as linker peptides.

The results shown in FIG. 8 indicate that ACTH (1-39), ACTH (1-41), (Glu) 10, dynorphin A, (Gly) 10, (Arg) 10, Cp6, C4a, BNP, bradykinin, HSA 237-249 fragment, C3f, ITIH4, HSA 397-413 fragment, HSA 599-609 fragment, C-peptide, and colistin are suitable as the linkers.

Example 3

(1) Hydrothermal Treatment

The TMR-labeled HSA 237-249 fragment, the TMR-labeled HSA 397-413 fragment or the TMR-labeled HSA 599-609 fragment was dissolved at a final concentration of 5 μM in 1 mL of phosphate buffered saline. Thus, a sample A (containing the TMR-labeled HSA 237-249 fragment), a sample B (containing the TMR-labeled HSA 397-413 fragment) or a sample C (containing the TMR-labeled HSA 599-609 fragment) was obtained.

First, 0.7 mL of the sample A was put in a screw cap bottle. Then, the uncovered screw cap bottle containing the sample A was placed in a heat transfer container made of iron. The hydrothermal treatment was performed in such a manner that the iron heat transfer container was heated in a thermostat bath at 200° C. for 40 minutes, and the iron heat transfer container was incubated until the temperature of the thermostat bath decreased to room temperature. The resulting solution was designated as a sample A after hydrothermal treatment. The hydrothermal treatment was performed in the same manner as described above except that the sample B or the sample C was used in place of the sample A in the above process.

(2) Preparation of Test Sample for SDS-PAGE

A test sample was produced in the same manner as in Example 2 (2) except that each of the samples A to C or each of the hydrothermally-treated samples was used in place of the TMR-labeled ACTH (1-24)-containing sample, the TMR-labeled ACTH (1-39)-containing sample or the supernatant after hydrothermal treatment of each of the samples in Example 2 (2).

(3) SDS-PAGE

The fluorescence image of the electrophoresis gel after SDS-PAGE was captured in the same manner as in Example 2 (3) except that the test sample obtained in Example 3 (2) was used in place of each of the test samples obtained in Example 2 (2).

Figure 9:
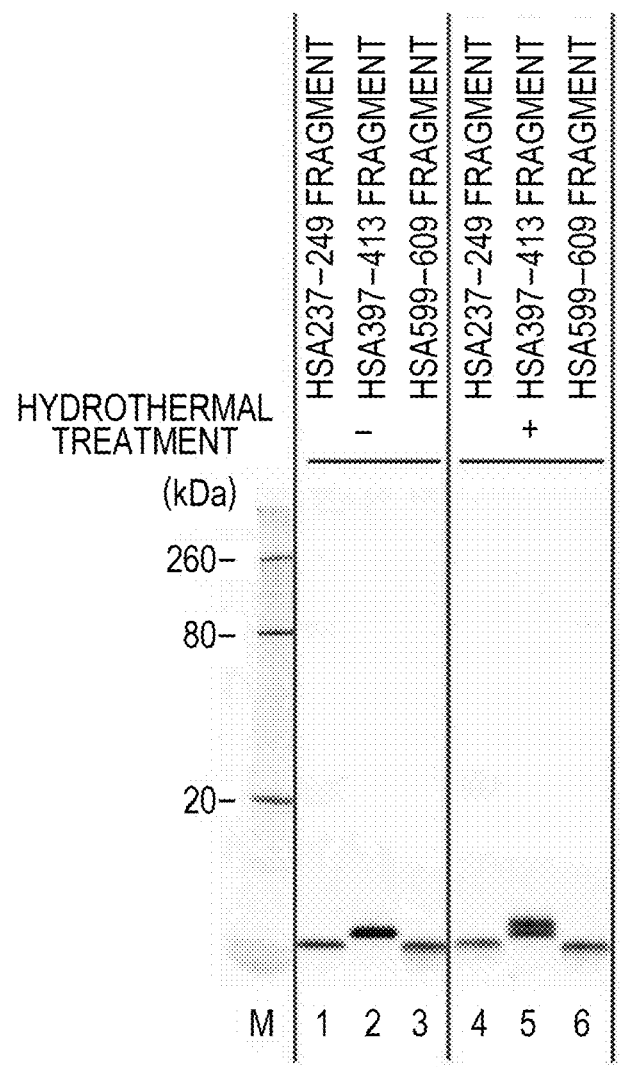
FIG. 9 is a photograph substituted for a drawing showing the electrophoresis gel after SDS-PAGE in Example 3.

FIG. 9 shows the results of SDS-PAGE performed in Example 3. In the photograph, Lane M represents the electrophoretic pattern of a molecular weight marker, Lane 1 represents the electrophoretic pattern of a sample A containing the untreated TMR-labeled HSA 237-249 fragment, Lane 2 represents the electrophoretic pattern of a sample B containing the untreated TMR-labeled HSA 397-413 fragment, Lane 3 represents the electrophoretic pattern of a sample C containing the untreated TMR-labeled HSA 599-609 fragment, Lane 4 represents the electrophoretic pattern of a sample A containing the hydrothermally-treated TMR-labeled HSA 237-249 fragment, Lane 5 represents the electrophoretic pattern of a sample B containing the hydrothermally-treated TMR-labeled HSA 397-413 fragment, and Lane 6 represents the electrophoretic pattern of a sample C containing the hydrothermally-treated TMR-labeled HSA 599-609 fragment.

From the results shown in FIG. 9, one band corresponding to each of the peptides was observed in Lanes 1 to 3 where the untreated peptides were used. On the other hand, in the case of Lanes 4 to 6 where the hydrothermally-treated peptides were used, two bands were observed only in Lane 5 where the hydrothermally-treated TMR-labeled HSA 397-413 fragment was used. Among the HSA 237-249 fragment, the HSA 397-413 fragment, and the HSA 599-609 fragment, only the HSA 397-413 fragment had an aspartic acid residue in the amino acid sequence. Therefore, the HSA 397-413 fragment was expected to be cleaved at the position of the aspartic acid residue by hydrothermal treatment. These

Comparative Example 1

(1) Hydrothermal Treatment

The TMR-labeled SA21 and HSA were dissolved at final concentrations of 8 μM and 300 μM, respectively, in 1 mL of phosphate buffered saline to obtain a TMR-labeled SA21-containing sample.

The hydrothermal treatment was performed in the same manner as in Example 3 (1) except that the TMR-labeled SA21-containing sample was used in place of the samples A to C in Example 3 (1).

As a result, the hydrothermally-treated TMR-labeled SA21-containing sample was separated into two phases: an insoluble fraction with red color (resulted from TMR) at the lower portion of the solution and a nearly clear and colorless supernatant. From this result, most of the TMR-labeled SA21 was expected to be present in the insoluble fraction.

The supernatant of the hydrothermally-treated TMR-labeled SA21-containing sample was collected.

(2) Preparation of Test Sample for SDS-PAGE

A test sample was produced in the same manner as in Example 2 (2) except that the untreated TMR-labeled SA21-containing sample or the supernatant of the hydrothermally-treated TMR-labeled SA21-containing sample was used in place of the TMR-labeled ACTH (1-24)-containing sample, the TMR-labeled ACTH (1-39)-containing sample or the supernatant after hydrothermal treatment of each of the samples in Example 2 (2).

(3) SDS-PAGE

SDS-PAGE was performed in the same manner as in Example 3 (3) except that the test sample obtained in Comparative example 1 (2) was used in place of each of the test samples obtained in Example 2 (2). The resulting electrophoresis gel was subjected to analysis with a fluorescence imager [product name: Pharos FX Molecular Imager, manufactured by Bio-Rad Laboratories, Inc.]. The fluorescence image of the electrophoresis gel was captured in High Sample Intensity mode at a wavelength for TAMRA (excitation wavelength: 532 nm). The resulting electrophoresis gel was silver-stained and a silver-stained image was captured.

Figure 10A:
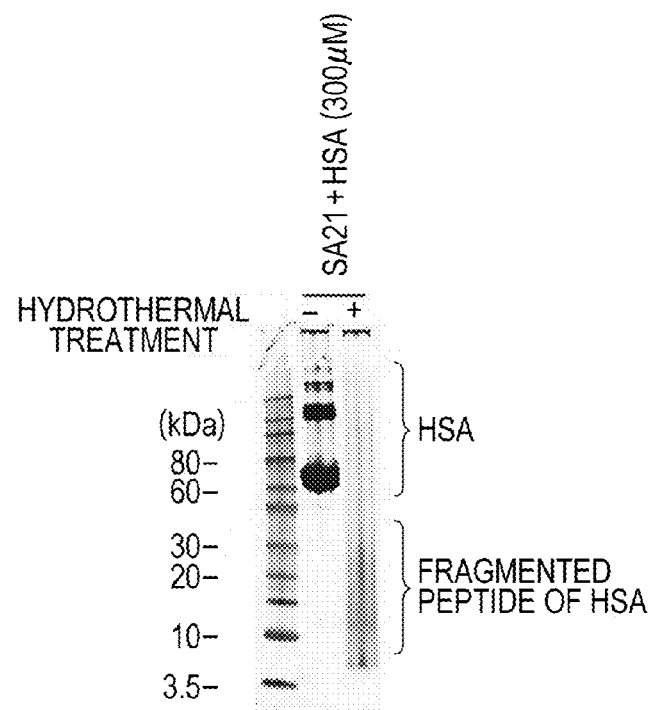
FIG. 10A is a photograph substituted for a drawing showing a silver-stained image of the electrophoresis gel after SDS-PAGE in Comparative example 1.
Figure 10B:
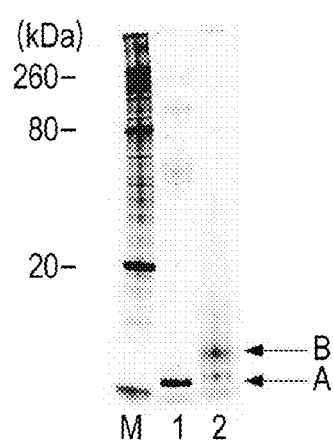
FIG. 10B is a photograph substituted for a drawing showing a fluorescence image of the electrophoresis gel after SDS-PAGE in Comparative example 1.

FIG. 10A shows a silver-stained image of the electrophoresis gel after SDS-PAGE in Comparative example 1, and FIG. 10B shows a fluorescence image of the electrophoresis gel after SDS-PAGE in Comparative example 1. In the photograph, Lane M represents the electrophoretic pattern of a molecular weight marker, Lane 1 represents the electrophoretic pattern of the untreated TMR-labeled SA1-containing sample, and Lane 2 represents the electrophoretic pattern of the supernatant of the hydrothermally-treated TMR-labeled SA21-containing sample. In the photograph, "A" represents a band derived from the untreated SA21 and "B" represents an aggregate of SA21.

From the results shown in FIG. 10A, a dark band derived from HSA was observed in the electrophoretic pattern of the untreated TMR-labeled SA1-containing sample (Lane 1). This result suggests that the untreated TMR-labeled SA1-containing sample contains a large amount of HSA. From the results shown in FIG. 10B, a band derived from the TMR-labeled SA1 was observed in the electrophoretic pattern of the untreated TMR-labeled SA1-containing sample (Lane 1).

On the other hand, from the results shown in FIG. 10A, a band derived from a fragmented peptide group, from which HSA was assumed to be fragmented, was observed in the electrophoretic pattern of the supernatant of the hydrothermally-treated TMR-labeled SA21-containing sample (Lane 2). From the results shown in FIG. 10B, a light band derived from the TMR-labeled SA21 was observed in the electrophoretic pattern of the supernatant of the hydrothermally-treated TMR-labeled SA21-containing sample (Lane 2). This result suggests that the supernatant of the hydrothermally-treated TMR-labeled SA21-containing sample contains a tiny amount of the TMR-labeled SA21.

These results suggest that most of the hydrothermally-treated HSA precipitates as an insoluble fraction, and a peptide with a low $K_d$ for HSA, i.e., a peptide having a high affinity for HSA is incorporated into the insoluble fraction. These results agreed with the results of the megascopic analysis of the supernatant after hydrothermal treatment and the insoluble fraction. Therefore, it is suggested that the peptide with a low $K_d$ for HSA is unsuitable as the linker of the peptide for temperature determination.

Example 4

(1) Hydrothermal Treatment

The TMR-labeled HSA 397-413 fragment was dissolved at a final concentration of 5 μM in 1 mL of phosphate buffered saline to obtain a sample D. The TMR-labeled HSA 599-609 fragment was dissolved at a final concentration of 5 μM in 1 mL of phosphate buffered saline to obtain a sample E. The TMR-labeled HSA 397-413 fragment and HSA were dissolved at final concentrations of 5 μM and 600 μM, respectively, in 1 mL of phosphate buffered saline to obtain a sample F. The TMR-labeled HSA 599-609 fragment and HSA were dissolved at final concentrations of 5 μM and 600 μM, respectively, in 1 mL of phosphate buffered saline to obtain a sample G. HSA was dissolved at a final concentration of 600 μM in 1 mL of phosphate buffered saline to obtain a control sample.

The hydrothermal treatment was performed in the same manner as in Example 3 (1) except that each of the samples D to G or the control sample was used in place of the samples A to C in Example 3 (1). The supernatant of each of the hydrothermally-treated samples was collected.

(2) Preparation of Test Sample for SDS-PAGE

A test sample was produced in the same manner as in Example 2 (2) except that each of the samples D to G, the control sample or the supernatant of each of the hydrothermally-treated samples was used in place of each of the test samples obtained in Example 2 (2).

(3) SDS-PAGE

The silver-stained and fluorescence images of the electrophoresis gel were captured in the same manner as in Comparative Example 1 (3) except that the test sample obtained in Example 4 (2) was used in place of each of the test samples obtained in Comparative Example 1 (2).

Figures 11A, 11B:
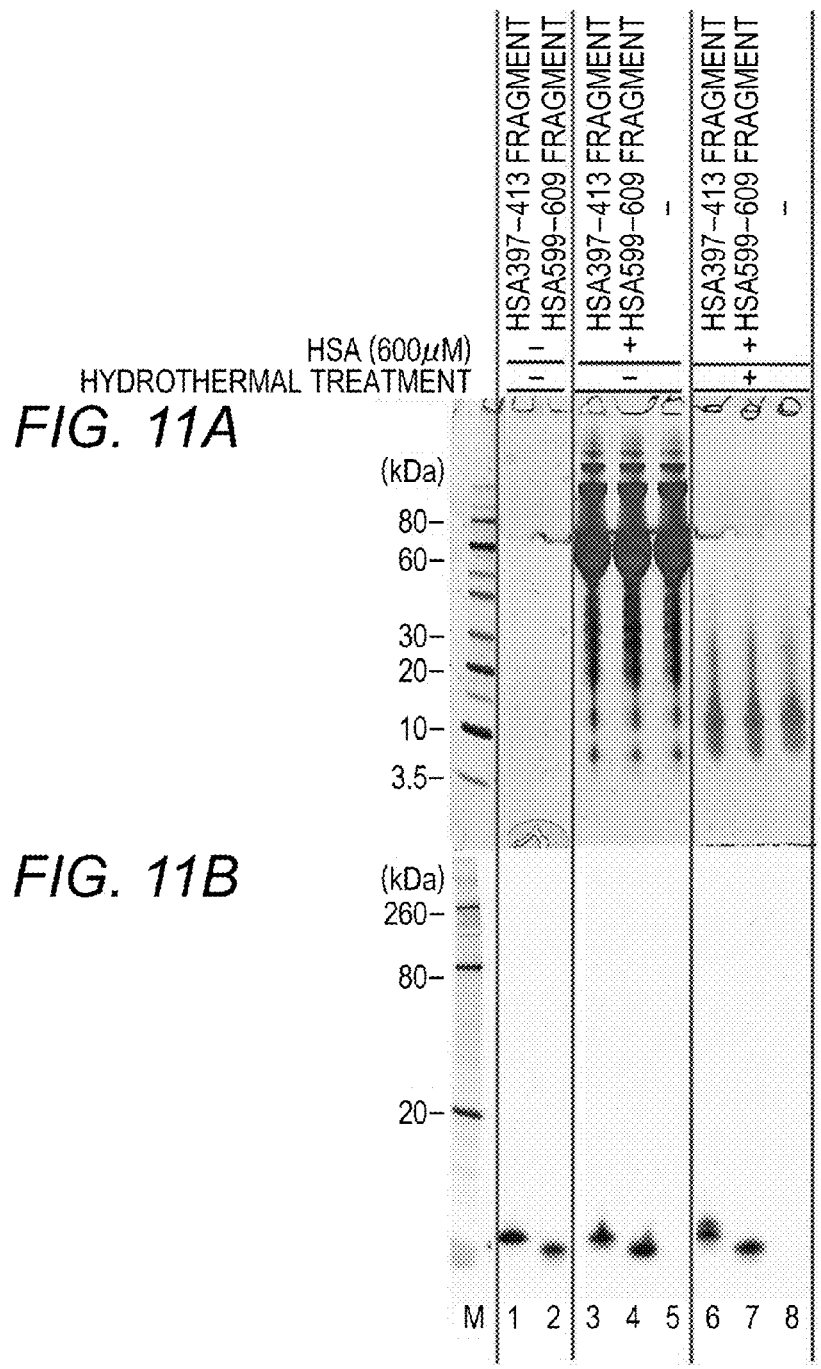
FIG. 11A is a photograph substituted for a drawing showing a silver-stained image of the electrophoresis gel after SDS-PAGE in Example 4.
FIG. 11B is a photograph substituted for a drawing showing a fluorescence image of the electrophoresis gel after SDS-PAGE in Example 4.

FIG. 11A shows a silver-stained image of the electrophoresis gel after SDS-PAGE in Example 4, and FIG. 11B shows a fluorescence image of the electrophoresis gel after SDS-PAGE in Example 4. In the photograph, Lane M represents the electrophoretic pattern of a molecular weight marker, Lane 1 represents the electrophoretic pattern of the untreated sample D, Lane 2 represents the electrophoretic pattern of the untreated sample E, Lane 3 represents the electrophoretic pattern of the untreated sample F, Lane 4 represents the electrophoretic pattern of the untreated sample G, Lane 5 represents the electrophoretic pattern of the untreated control sample, Lane 6 represents the electrophoretic pattern of the supernatant of the hydrothermally-treated sample F, Lane 7 represents the electrophoretic pattern of the supernatant of the hydrothermally-treated sample F, and Lane 8 represents the electrophoretic pattern of the supernatant of the hydrothermally-treated control sample.

From the results shown in FIG. 11A, dark bands derived from HSA were observed in the electrophoretic patterns of the untreated sample F, sample G, and control sample (Lanes 3 to 5). Bands derived from the fragmented peptide group, from which HSA was assumed to be fragmented, were observed in the electrophoretic patterns of the supernatants of the hydrothermally-treated sample F, sample G, and control sample (Lanes 6 to 8).

On the other hand, from the results shown in FIG. 11B, bands derived from the TMR-labeled HSA 397-413 fragment were observed in the electrophoretic pattern of the untreated sample F (Lane 3) and the electrophoretic pattern of the sample F after hydrothermal treatment (Lane 6). Bands derived from the TMR-labeled HSA 599-609 fragment were observed in the electrophoretic pattern of the supernatant of the untreated sample G (Lane 4) and the electrophoretic pattern of the supernatant of the sample G after hydrothermal treatment (Lane 7). On the other hand, no band derived from peptide was observed in the electrophoretic pattern of the control sample (Lane 5).

These results indicate that a peptide with a high $K_d$ for HSA (with a $K_d$ of 500 μM or more for HSA), i.e., a peptide having a low affinity for HSA is incorporated into the insoluble fraction after hydrothermal treatment. Therefore, these results suggest that the peptide with a high $K_d$ for HSA is suitable as the linker peptide of the peptide for temperature determination.

Example 5

(1) Preparation of Untreated Sample

DABCYL-HSA 397-413 fragment-EDANS in which both the termini of the HSA 397-413 fragment (N- and C-termini) were labeled was dissolved at a final concentration of 20 μM in 6 mL of 100 mM glycine-hydrochloride buffer (pH 2.5) to obtain a sample H. The DABCYL-HSA 397-413 fragment-EDANS was designed such that the fluorescence from EDANS in a non-cleaved state was quenched by DABCYL and the intensity of the fluorescence from EDANS was increased by cleavage of the EDANS.

(2) Hydrothermal Treatment

First, 1.5 mL of the sample H obtained in Example 5 (1) was placed in a glass container for hydrothermal treatment. Then, the glass container for hydrothermal treatment containing the sample H was put in a microwave synthesis reactor [product name: MultiSYNTH, manufactured by Milestone General K.K.] and the hydrothermal treatment was performed at 80° C., 120° C. or 160° C. under the conditions shown in Table 4.

TABLE 4

| Hydrothermal treatment | Temperature conditions |
|---|---|
| 80° C. | Increase temperature from room temperature (25° C.) to 80° C. over 30 seconds<br>Incubate at 80° C. for 10 seconds<br>Cool to room temperature |
| 120° C. | Increase temperature from room temperature (25° C.) to 100° C. over 30 seconds<br>Increase temperature from 100° C. to 120° C. over 60 seconds<br>Incubate at 120° C. for 10 seconds<br>Cool to room temperature |
| 160° C. | Increase temperature from room temperature (25° C.) to 100° C. over 30 seconds<br>Increase temperature from 100° C. to 160° C. over 60 seconds<br>Incubate at 160° C. for 10 seconds<br>Cool to room temperature |

(3) Measurement of Fluorescence Spectrum

The untreated sample H obtained in Example 5 (1) and the hydrothermally-treated sample H obtained in Example 5 (2) were subjected to measurement with a spectrophotofluorometer [product name: F-7000, manufactured by Hitachi High-Technologies Corporation] and the fluorescence spectrum with an excitation wavelength of 335 nm and a fluorescence wavelength of 360 to 600 nm was measured.

Figure 12:
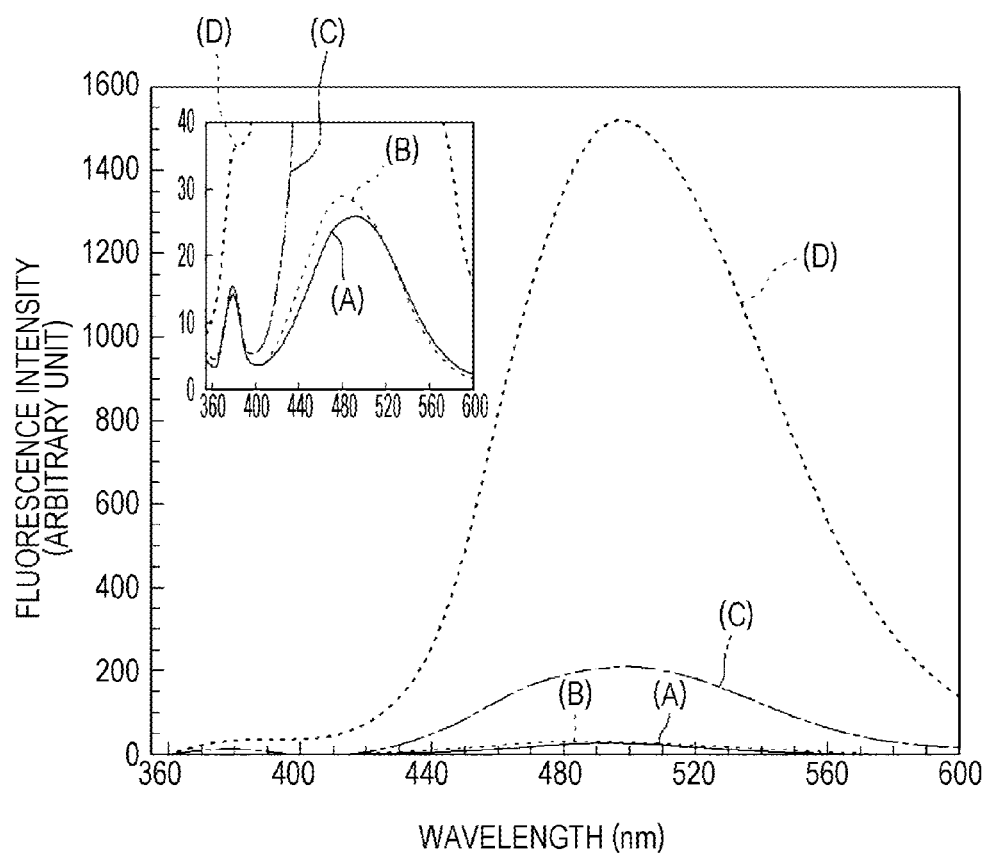
FIG. 12 is a spectrum showing the results of the measurement of the fluorescence spectrum with an excitation wavelength of 335 nm and a fluorescence wavelength of 360 to 600 nm regarding the untreated sample and each of the hydrothermally-treated samples in Example 5.
Figure 13:
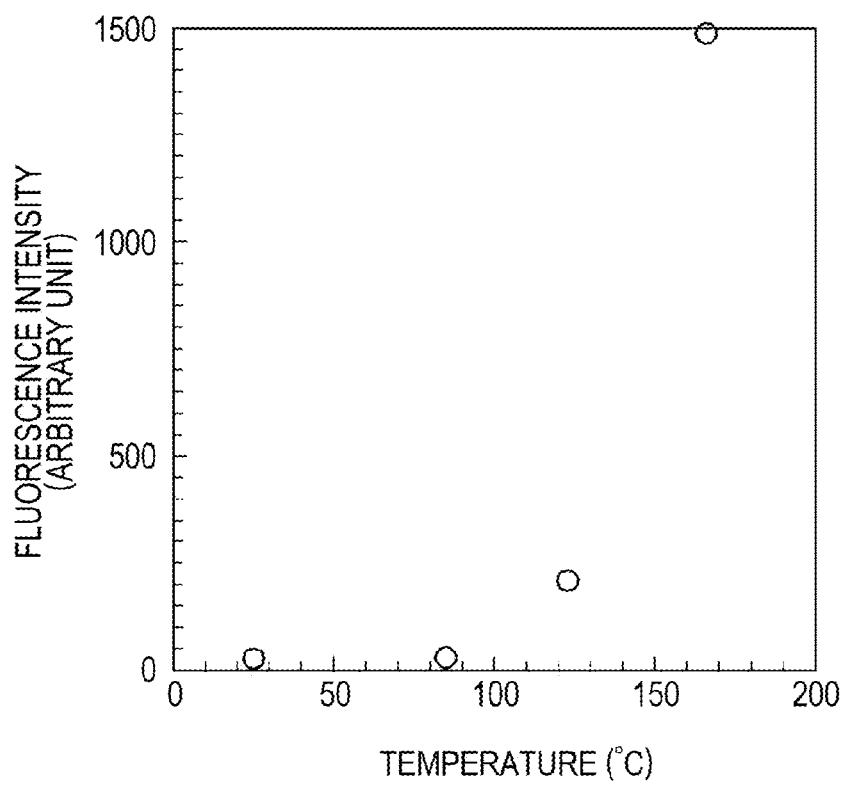
FIG. 13 is a graph showing the analyzed results of the relationship between the fluorescence intensity with an excitation wavelength of 335 nm and a fluorescence wavelength of 490 nm and the heating temperature in the hydrothermal treatment regarding the untreated sample and each of the hydrothermally-treated samples in Example 5.

FIG. 12 shows the results of the measurement of the fluorescence spectrum with an excitation wavelength of 335 nm and a fluorescence wavelength of 360 to 600 nm regarding the untreated sample and each of the hydrothermally-treated samples in Example 5. In the graph, (A) represents a fluorescence spectrum of the untreated sample H, (B) represents a fluorescence spectrum of the sample H hydrothermally treated at 80° C., (C) represents a fluorescence spectrum of the sample H hydrothermally treated at 160° C., and (D) represents a fluorescence spectrum of the sample H hydrothermally treated at 160° C. FIG. 13 shows the analyzed results of the relationship between the fluorescence intensity with an excitation wavelength of 335 nm and a fluorescence wavelength of 490 nm and the heating temperature in the hydrothermal treatment regarding the untreated sample and each of the hydrothermally-treated samples.

The results shown in FIGS. 12 and 13 indicate that when the hydrothermal treatment is performed at 120° C. or more, the fluorescence intensity is increased. Therefore, these results suggest that when the hydrothermal treatment is performed at 120° C. or more, the HSA 397-413 fragment is cleaved.

(4) Preparation of Test Sample for SDS-PAGE

A test sample was produced in the same manner as in Example 3 (1) except that the untreated sample H obtained in Example 5 (1) or the hydrothermally-treated sample H obtained in Example 5 (2) was used in place of each of the samples A to C or each of the hydrothermally-treated samples in Example 3 (1).

(5) SDS-PAGE

Figure 14:
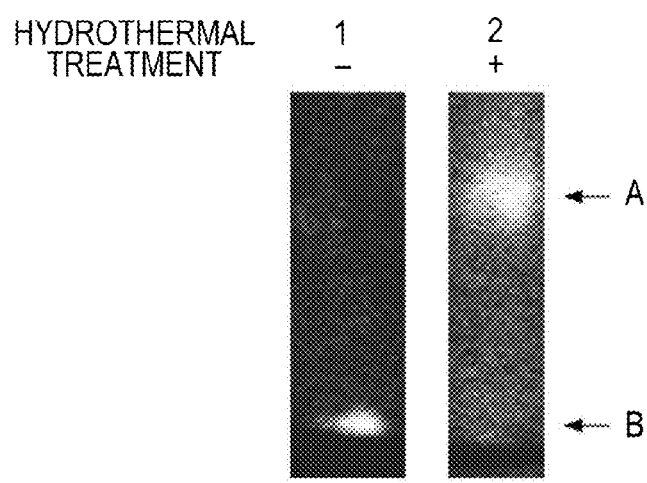
FIG. 14 is a photograph substituted for a drawing showing fluorescence images of electrophoresis gels after SDS-PAGE regarding the untreated DABCYL-HSA 397-413 fragment-EDANS and the product after hydrothermal treatment of DABCYL-HSA 397-413 fragment-EDANS in Example 5.

SDS-PAGE was performed in the same manner as in Example 2 (3) except that the test sample obtained in Example 5 (4) was used in place of each of the test samples obtained in Example 2 (2). The gel after electrophoresis was irradiated with UV light using a transilluminator (model: NM-15 95-0219-03, manufactured by UVP), and a photograph of the gel was taken with a camera (COOLPIX 4500, manufactured by Nikon Corporation) equipped with an orange filter. Thus, the electrophoretic pattern of only the fluorescence image with the excitation light removed was visualized. The cleaved state of the DABCYL-HSA 397-413 fragment-EDANS by hydrothermal treatment was confirmed based on the position of a band emitting fluorescence from EDANS. FIG. 14 shows fluorescence images of electrophoresis gels after SDS-PAGE regarding the untreated DABCYL-HSA 397-413 fragment-EDANS and the product after hydrothermal treatment of DABCYL-HSA 397-413 fragment-EDANS in Example 5. In the photograph, Lane 1 represents the electrophoretic pattern of the untreated DABCYL-HSA 397-413 fragment-EDANS and Lane 2 represents the electrophoretic pattern of the product after hydrothermal treatment of DABCYL-HSA 397-413 fragment-EDANS.

From the results shown in FIG. 14, only a band derived from the untreated DABCYL-HSA 397-413 fragment-EDANS (arrow A) was observed in Lane 1. On the other hand, the band derived from the untreated DABCYL-HSA 397-413 fragment-EDANS was not observed in Lane 2, but a band corresponding to the peptide having a lower molecular weight was observed. These results suggest that the HSA 397-413 fragment is cleaved by hydrothermal treatment.

Example 6

(1) Preparation of Untreated Sample

A sample I was produced in the same manner as in Example 5 (1) except that a 50 µM pH 11 CAPS-sodium hydroxide buffer was used in place of a 100 mM glycine-hydrochloride buffer (pH 2.5) in Example 5 (1).

(2) Hydrothermal Treatment

The hydrothermal treatment at 160° C. was performed in the same manner as in Example 5 (2) except that the sample I obtained in Example 6 (1) was used in place of the sample H obtained in Example 5 (1).

(3) Measurement of Fluorescence Intensity

While the container containing the untreated sample I obtained in Example 6 (1) and the container containing the hydrothermally-treated sample I obtained in Example 6 (2) were irradiated with UV light using a transilluminator (model: NM-15 95-0219-03, manufactured by UVP), a photograph of the gel was taken with a camera (COOLPIX 4500, manufactured by Nikon Corporation) equipped with an orange filter. Thus, the fluorescence image with the excitation light removed was visualized. The resulting image and image processing software [product name: Image J, provided by National Institute of Health] were used to quantify the intensity of the fluorescence resulting from the cleavage of DABCYL-HSA 397-413 fragment-EDANS as a gray value.

Figure 15:
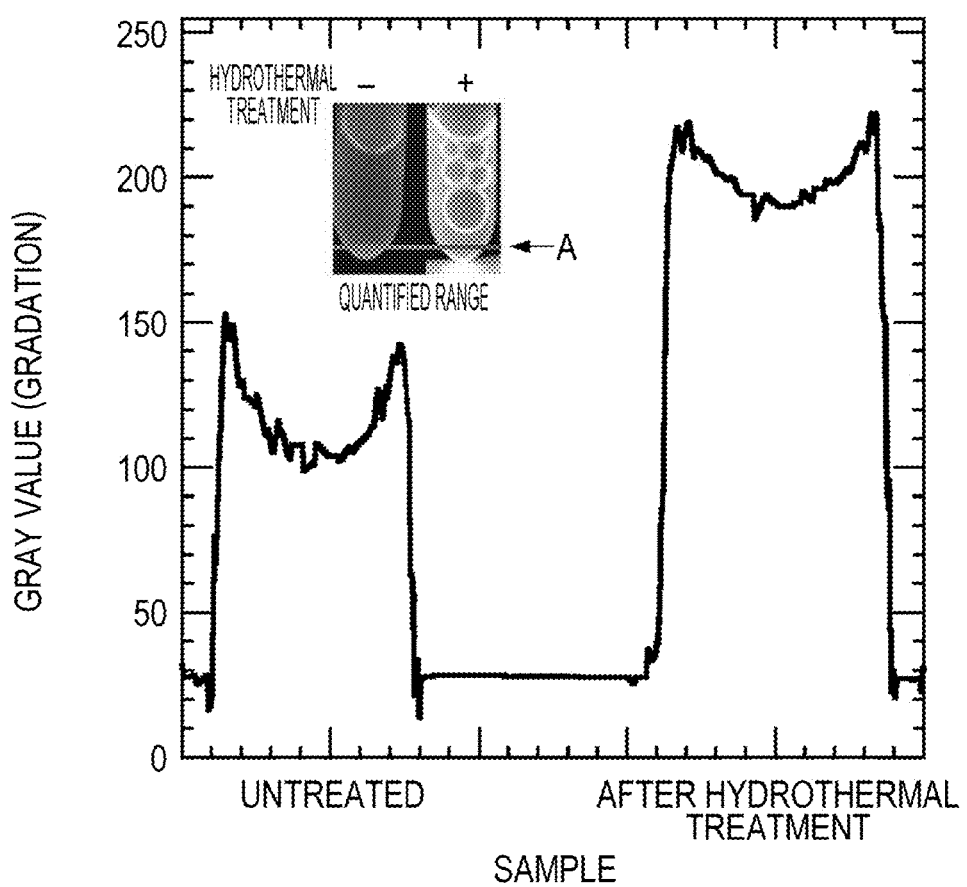
FIG. 15 is a graph showing the results obtained by quantifying the intensity of the fluorescence resulting from the cleavage of DABCYL-HSA 397-413 fragment-EDANS as a gray value, regarding the untreated sample and each of the hydrothermally-treated samples in Example 6.

FIG. 15 shows the results obtained by quantifying the intensity of the fluorescence resulting from the cleavage of DABCYL-HSA 397-413 fragment-EDANS as a gray value, regarding the untreated sample and each of the hydrothermally-treated samples in Example 6. In the graph in FIG. 15, the fluorescence intensity at the position indicated by an arrow A in the photograph in FIG. 15 is quantified as a gray value.

The results shown in FIG. 15 indicate that when the hydrothermal treatment at 160° C. was performed under alkaline conditions (pH 11), the fluorescence intensity was increased compared with the case where the sample was not treated. These results suggest that an increase in the fluorescence intensity resulting from the cleavage of DABCYL-HSA 397-413 fragment-EDANS by hydrothermal treatment is an indicator for determining whether the heating temperature reached the predetermined temperature. Therefore, it is suggested that the DABCYL-HSA 397-413 fragment-EDANS can be used as the peptide for temperature determination.

Example 7

(1) Preparation of Untreated Sample

MCA-HSA 397-413 fragment-DNP in which both the termini of the HSA 397-413 fragment (N- and C-termini) were labeled was dissolved at a final concentration of 20 µM in 6 mL of phosphate buffered saline to obtain a sample J. The MCA-HSA 397-413 fragment-DNP was designed such that the fluorescence from DNP in a non-cleaved state was quenched by MCA and the intensity of the fluorescence from DNP was increased by cleavage of the DNP.

(2) Hydrothermal Treatment

The hydrothermal treatment at 160° C. was performed in the same manner as in Example 5 (2) except that the sample J obtained in Example 7 (1) was used in place of the sample H obtained in Example 5 (1).

(3) Measurement of Fluorescence Intensity

The intensity of the fluorescence resulting from the cleavage of MCA-HSA 397-413 fragment-DNP was quantified as a gray value in the same manner as in Example 6 (3) except that the container containing the untreated sample J obtained in Example 7 (1) and the container containing the hydrothermally-treated sample J obtained in Example 7 (2) were used in place of the container containing the untreated sample I and the container containing the hydrothermally-treated sample I in Example 6 (3).

Figure 16:
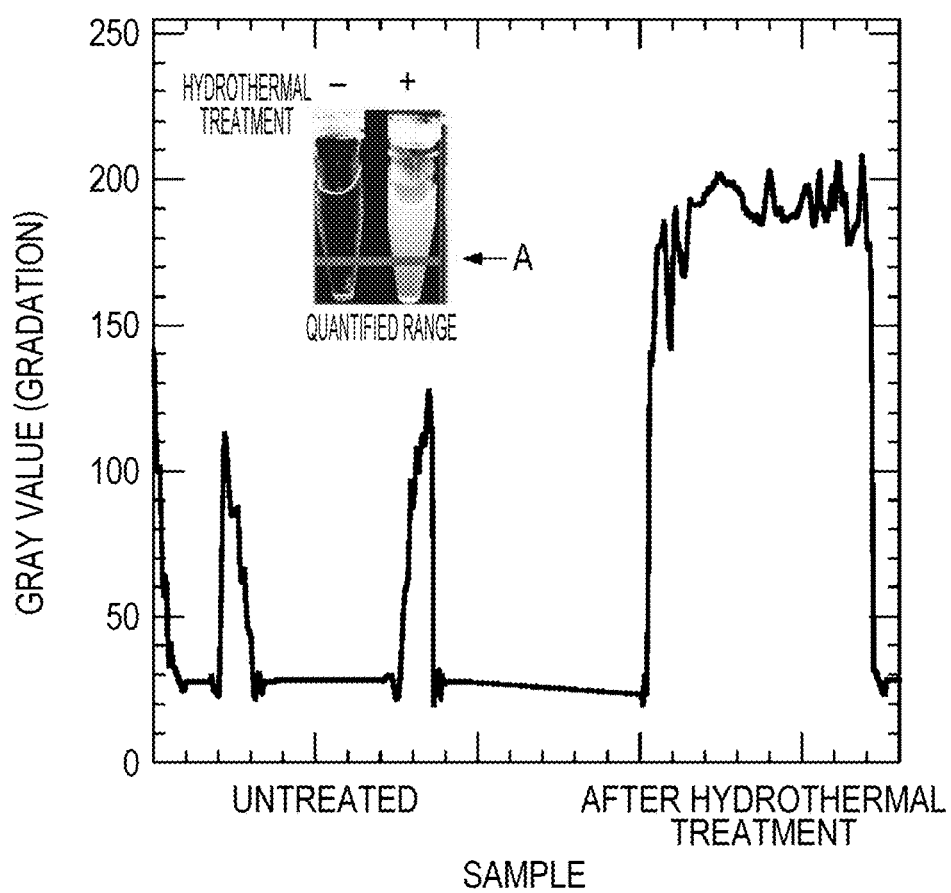
FIG. 16 is a graph showing the results obtained by quantifying the intensity of the fluorescence resulting from the cleavage of MCA-HSA 397-413 fragment-DNP as a gray value in Example 7.

FIG. 16 shows the results obtained by quantifying the intensity of the fluorescence resulting from the cleavage of MCA-HSA 397-413 fragment-DNP as a gray value in Example 7. In the graph in FIG. 16, the fluorescence intensity at the position indicated by an arrow A in the photograph in FIG. 16 is quantified as a gray value.

The results shown in FIG. 16 indicate that when the MCA-HSA 397-413 fragment-DNP was hydrothermally treated at 160° C. under neutral conditions (pH 7.5), the fluorescence intensity was increased compared with the case where the sample was not treated. These results suggest that an increase in the fluorescence intensity resulting from the cleavage of MCAHSA 397-413 fragment-DNP by hydrothermal treatment is an indicator for determining whether the heating temperature reached the predetermined temperature. Therefore, it is suggested that the MCA-HSA 397-413 fragment-DNP can be used as the peptide for temperature determination.

Example 8

(1) Preparation of Untreated Sample

DABCYL-HSA 397-413 fragment-EDANS and HSA were dissolved at final concentrations of 20 µM and 300 µM, respectively, in 1.5 mL of phosphate buffered saline to obtain a sample K.

(2) Hydrothermal Treatment

The hydrothermal treatment at 160° C. was performed in the same manner as in Example 5 (2) except that the sample K obtained in Example 8 (1) was used in place of the sample H obtained in Example 5 (1).

(3) Measurement of Fluorescence Intensity

The intensity of the fluorescence resulting from the cleavage of DABCYL-HSA 397-413 fragment-EDANS and HSA was quantified as a gray value in the same manner as in Example 6 (3) except that the container containing the untreated sample K obtained in Example 8 (1) and the container containing the hydrothermally-treated sample K obtained in Example 8 (2) were used in place of the container containing the untreated sample I and the container containing the hydrothermally-treated sample I in Example 6 (3).

Figure 17A:
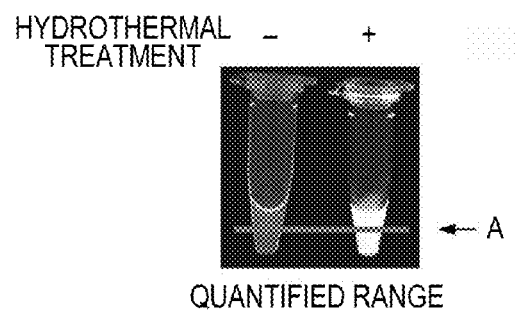
FIG. 17A is a photograph substituted for a drawing showing the results obtained by observing a container containing an untreated sample and a container containing a hydrothermally-treated sample in Example 8.
Figure 17B:
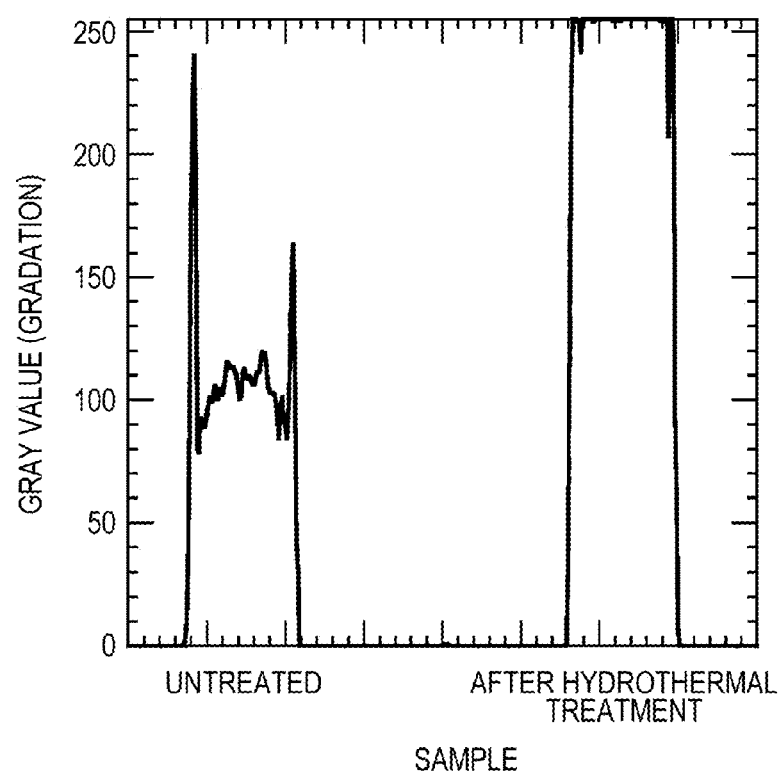
FIG. 17B is a graph showing the results obtained by quantifying the intensity of the fluorescence resulting from the cleavage of DABCYL-HSA 397-413 fragment-EDANS as a gray value in Example 8.

FIG. 17A shows the results obtained by observing a container containing the untreated sample and the container containing the hydrothermally-treated sample in Example 8, and FIG. 17B shows the results obtained by quantifying the intensity of the fluorescence resulting from the cleavage of DABCYL-HSA 397-413 fragment-EDANS as a gray value in Example 8. In the graph in FIG. 17B, the fluorescence intensity at the position indicated by an arrow A in the photograph in FIG. 17A is quantified as a gray value.

The results shown in FIG. 17 indicate that when the hydrothermal treatment was performed in the presence of HSA, the fluorescence intensity was increased compared with the case where the sample was not treated in the presence of HSA. Therefore, these results suggest that the DABCYL-HSA 397-413 fragment-EDANS can be used as the peptide for temperature determination even in the presence of a contaminating protein such as HSA.

Example 9

(1) Preparation of Untreated Sample

DABCYL-HSA 397-413 fragment-EDANS, whole blood [product name: EDTA Whole blood (20 year-old female), manufactured by PROMEDDX, LLC], and glycine were prepared to produce a 3 mL solution having final concentrations of 60 µM, 5-fold dilution, and 1 M, respectively to obtain a sample L.

(2) Hydrothermal Treatment

The hydrothermal treatment at 160° C. was performed in the same manner as in Example 5 (2) except that the sample L obtained in Example 9 (1) was used in place of the sample H obtained in Example 5 (1).

(3) Evaluation of Untreated Sample and Hydrothermally-Treated Sample

The untreated sample L and the hydrothermally-treated sample L were subjected to centrifugation at 15000×g for 3 minutes. The container containing the resulting supernatant was photographed under visible light. While the container containing the resulting supernatant was irradiated with UV light using a transilluminator (model: NM-15 95-0219-03, manufactured by UVP), a photograph of the container was taken with a camera (COOLPIX 4500, manufactured by Nikon Corporation) through an orange filter. The image photographed under UV irradiation and image processing software [product name: Image J, provided by National Institute of Health] were used to quantify the intensity of the fluorescence resulting from the cleavage of DABCYL-HSA 397-413 fragment-EDANS as a gray value.

Figure 18A:
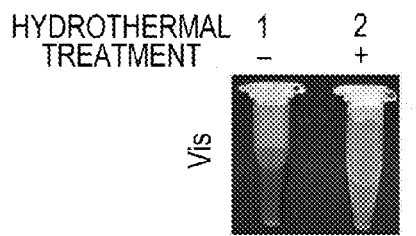
FIG. 18A is a photograph substituted for a drawing showing the results of a container containing an untreated sample and a container containing a hydrothermally-treated sample which were observed under visible light in Example 9.
Figure 18B:
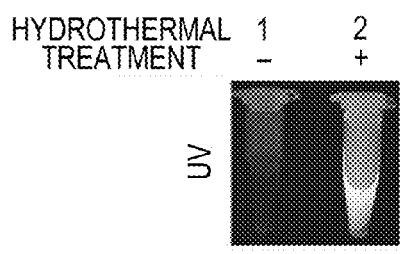
FIG. 18B is a photograph substituted for a drawing showing the results of a container containing an untreated sample and a container containing a hydrothermally-treated sample which were observed under ultraviolet irradiation in Example 9.
Figure 18C:
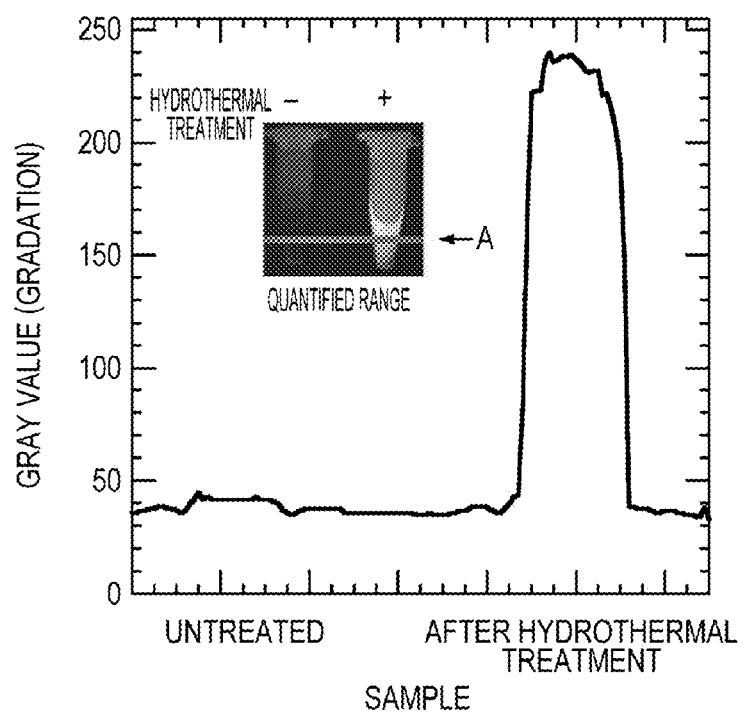
FIG. 18C is a photograph substituted for a drawing showing the results obtained by quantifying the intensity of the fluorescence resulting from the cleavage of DABCYL-HSA 397-413 fragment-EDANS as a gray value in Example 9.

FIG. 18A shows the results of the container containing the untreated sample and the container containing the hydrothermally-treated sample which were observed under visible light in Example 9, FIG. 18B shows the results of the container containing the untreated sample and the container containing the hydrothermally-treated sample which were observed under ultraviolet irradiation in Example 9, and FIG. 18C shows the results obtained by quantifying the intensity of the fluorescence resulting from the cleavage of DABCYL-HSA 397-413 fragment-EDANS as a gray value in Example 9. In the graph in FIG. 18C, the fluorescence intensity at the position indicated by an arrow A in the photograph in the graph is quantified as a gray value.

The results shown in FIG. 18 indicate that when the hydrothermal treatment was performed in the presence of whole blood, the fluorescence intensity was increased compared with the case where the sample was not treated in the presence of whole blood. Therefore, these results suggest that DABCYL-HSA 397-413 fragment-EDANS can be used as the peptide for temperature determination even in the presence of a biological sample containing a large amount of contaminating proteins, such as whole blood.

Example 10

(1) Preparation of Untreated Sample

DABCYL-HSA 397-413 fragment-EDANS and TMR-SA21 were dissolved at final concentrations of 200 µM and 20 µM, respectively, in 0.1-fold phosphate buffered saline. Then, 750 µL of the resulting solution and 300 µL of serum from a healthy woman (22 years old) [product name: Normal Serum Pool, manufactured by PROMEDDX, LLC] were mixed. To 1050 µL of the resulting serum-containing solution, 375 µL of 2 M glycine solution and 75 µL of phosphate buffered saline were added to obtain a sample M.

(2) Hydrothermal Treatment

The hydrothermal treatment at 160° C. was performed in the same manner as in Example 5 (2) except that the sample M obtained in Example 9 (1) was used in place of the sample H obtained in Example 5 (1).

(3) Evaluation of Untreated Sample and Hydrothermally-Treated Sample

The container containing the untreated sample M and the container containing the hydrothermally-treated sample M were photographed under visible light. As a result, it was confirmed that an insoluble fraction was attached to the wall surface of the container. It was confirmed that the insoluble fraction exhibited a red color derived from TMR. The data image of only the red channel was obtained from the resulting image using image processing software [product name: Photoshop, manufactured by Adobe Systems Software Ireland Ltd.]. The data image of only the resulting red channel and image processing software [product name: Image J, provided by National Institute of Health] were used to quantify the intensity of the fluorescence resulting from the cleavage of DABCYL-HSA 397-413 fragment-EDANS as a gray value.

Figure 19A:
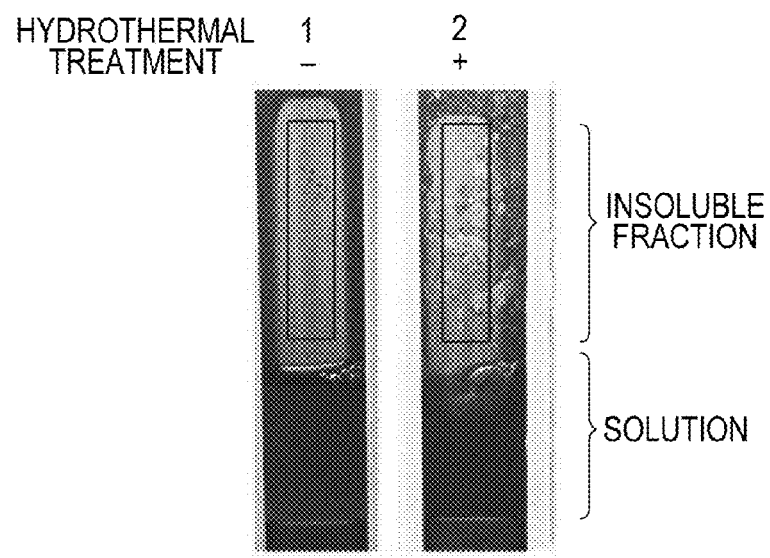
FIG. 19A is a photograph substituted for a drawing showing the results of a container containing an untreated sample and a container containing a hydrothermally-treated sample which were observed under visible light in Example 10.
Figure 19B:
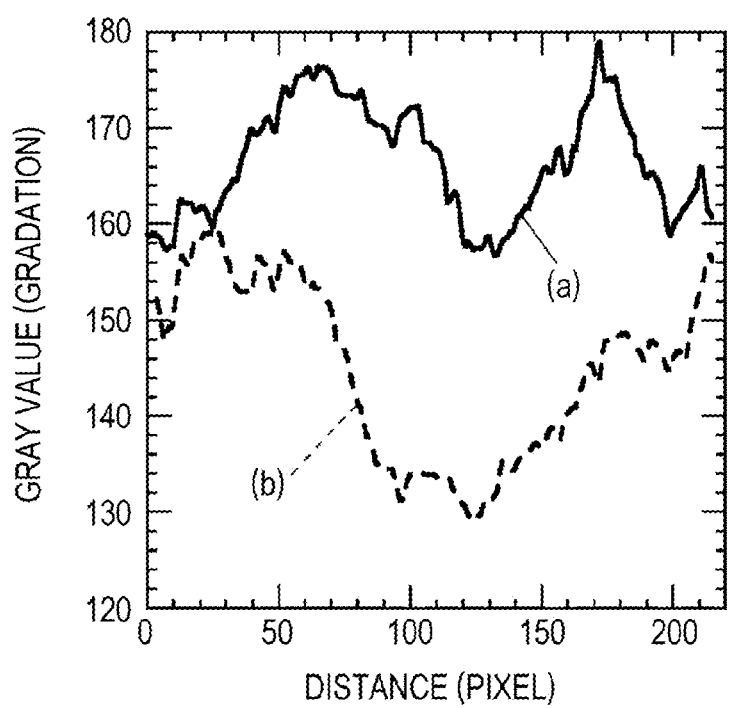
FIG. 19B is a graph showing the results obtained by quantifying the intensity of the fluorescence resulting from the cleavage of DABCYL-HSA 397-413 fragment-EDANS as a gray value in Example 10.

FIG. 19A shows the results of the container containing the untreated sample and the container containing the hydrothermally-treated sample which were observed under visible light in Example 10, and FIG. 19B shows the results obtained by quantifying the intensity of the fluorescence resulting from the cleavage of DABCYL-HSA 397-413 fragment-EDANS as a gray value in Example 10. In FIG. 19B, (a) represents the hydrothermally-treated sample and the dashed line (b) represents the untreated sample. In the graph in FIG. 19B, the fluorescence intensities of the boxed portions in the photograph in FIG. 19A were quantified as a gray value.

Then, only the supernatant was transferred to an Eppendorf tube. While the Eppendorf tube including the supernatant was irradiated with UV light using a transilluminator (model: NM-15 95-0219-03, manufactured by UVP), a photograph of the tube was taken with a camera (COOLPIX 4500, manufactured by Nikon Corporation) equipped with an orange filter. Thus, a UV excitation image was obtained. The image photographed under UV irradiation and image processing software [product name: Image J, provided by National Institute of Health] were used to quantify the intensity of the fluorescence resulting from the cleavage of DABCYL-HSA 397-413 fragment-EDANS as a gray value.

Figure 20A:
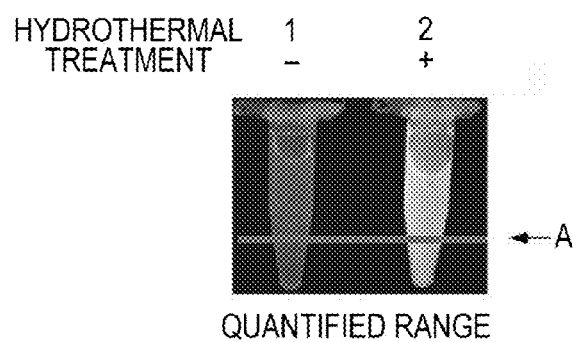
FIG. 20A is a photograph substituted for a drawing showing the results of a container containing an untreated sample and a container containing a hydrothermally-treated sample which were observed under ultraviolet irradiation in Example 10.
Figure 20B:
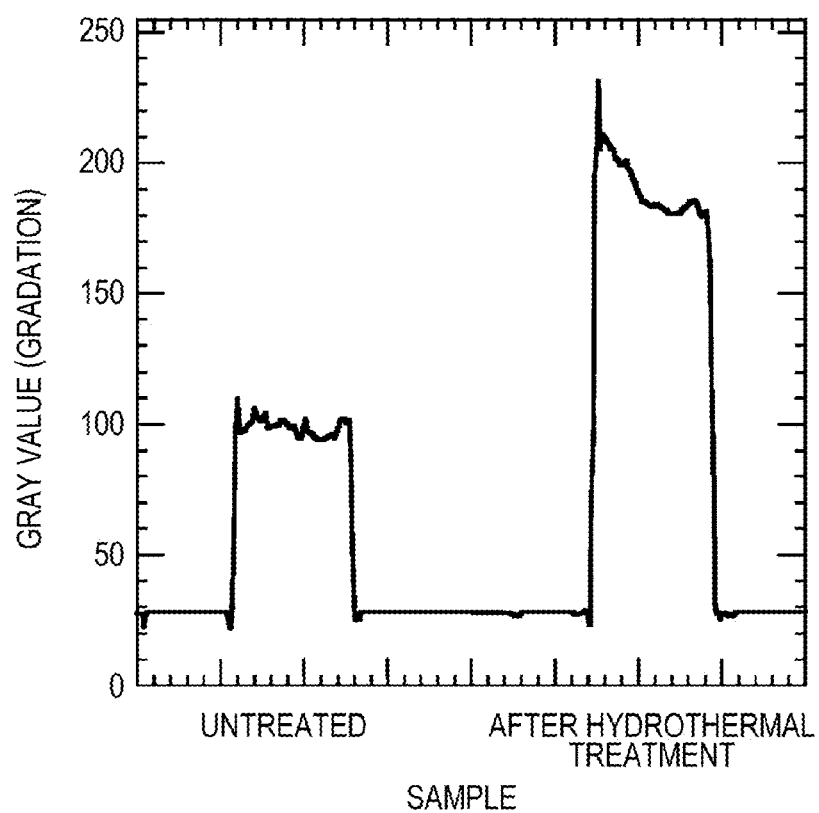
FIG. 20B is a graph showing the results obtained by quantifying the intensity of the fluorescence resulting from the cleavage of DABCYL-HSA 397-413 fragment-EDANS as a gray value in Example 10.

FIG. 20A shows the results of the container containing the untreated sample and the container containing the hydrothermally-treated sample which were observed under ultraviolet irradiation in Example 10, and FIG. 20B shows the results obtained by quantifying the intensity of the fluorescence resulting from the cleavage of DABCYL-HSA 397-413 fragment-EDANS as a gray value in Example 10. In the graph in FIG. 20B, the fluorescence intensity at the position indicated by an arrow A in the photograph in FIG. 20A is quantified as a gray value.

The results shown in FIG. 19 indicate that the insoluble fraction attached to the surface of the glass tube exhibited a red color derived from TMR. The results shown in FIG. 20 indicate that when the hydrothermal treatment was performed, the fluorescence from EDANS was enhanced compared with the case where the sample was not treated. These results suggest that HSA in the serum was bound to TMR-SA21 by hydrothermal treatment, TMR-SA21 was transferred to the insoluble fraction, and DABCYL-HSA 397-413 fragment-EDANS was cleaved in the supernatant. SA21 had a $K_d$ of less than 500 μM for HSA and was a peptide having a high affinity for HSA. Therefore, these results suggest that the peptide having a high affinity for HSA can be used as the peptide for phase partition determination to determine whether HSA is precipitated as an insoluble fraction.

Sequence Listing Free Text

SEQ ID NO: 1 is a sequence of β-amyloid (1-40) fragment.
SEQ ID NO: 2 is a sequence of β-amyloid (1-42) fragment.
SEQ ID NO: 3 is a sequence of RSA21.
SEQ ID NO: 4 is a sequence of glucagon (1-29).
SEQ ID NO: 5 is a sequence of ACTH (7-11).
SEQ ID NO: 6 is a sequence of (Lys) 10.
SEQ ID NO: 7 is a sequence of kininogen.
SEQ ID NO: 8 is a sequence of C3f (16 amino acid residues).
SEQ ID NO: 9 is a sequence of SA21.
SEQ ID NO: 10 is a sequence of ACTH (2-16).
SEQ ID NO: 11 is a sequence of (His)3.
SEQ ID NO: 12 is a sequence of fibrinogen α.
SEQ ID NO: 13 is a sequence of lqp.
SEQ ID NO: 14 is a sequence of ACTH (1-24).
SEQ ID NO: 15 is a sequence of blood coagulation factor XIII.
SEQ ID NO: 16 is a sequence of ACTH (1-39).
SEQ ID NO: 17 is a sequence of ACTH (1-41).
SEQ ID NO: 18 is a sequence of (Glu) 10.
SEQ ID NO: 19 is a sequence of dynorphin A.
SEQ ID NO: 20 is a sequence of (Gly) 10.
SEQ ID NO: 21 is a sequence of (Arg) 10.
SEQ ID NO: 22 is a sequence of Cp6.
SEQ ID NO: 23 is a sequence of C4a.
SEQ ID NO: 24 is a sequence of BNP.
SEQ ID NO: 25 is a sequence of bradykinin.
SEQ ID NO: 26 is a sequence of HSA 237-249 fragment.
SEQ ID NO: 27 is a sequence of C3f (8 amino acid residues).
SEQ ID NO: 28 is a sequence of ITIH4.
SEQ ID NO: 29 is a sequence of HSA 397-413 fragment.
SEQ ID NO: 30 is a sequence of HSA 599-609 fragment.
SEQ ID NO: 31 is a sequence of C-peptide.
SEQ ID NO: 32 is a sequence of colistin. Xaa at position 4 is 6-methyl-1-oxooctyl-Dbu or 6-methyl-1-oxoheptyl-Dbu. Xaa at positions 3, 4, 5, 8 and 9 is Dbu. Xaa at position 4 and Thr at position 10 are bound to each other to form a ring. Leu at position 6 is D-leucine. Thr at position 10 is not a terminus.

What is claimed is:

1. A method of determining whether a temperature of a sample has reached a predetermined temperature, said predetermined temperature being a temperature between 120° C. and 250° C., comprising the steps of:
mixing an albumin-containing sample with a peptide reagent comprising a peptide for temperature determination;
heating the mixture;
detecting an optical change of the mixture; and
determining whether the temperature of the mixture has reached the predetermined temperature based on the detection result of the optical change,
wherein a dissociation constant ($K_d$) of binding of the peptide for temperature determination to albumin is 500 μM or more,
wherein the peptide for temperature determination comprises a first labeling substance and a second labeling substance, wherein the first labeling substance is an energy donor and the second labeling substance is a quencher or acceptor,
wherein the peptide for temperature determination comprises at least one amino acid residue selected from the group consisting of aspartic acid, glutamic acid, asparagine, serine, glycine, leucine, alanine, proline, and lysine residues,
wherein the at least one amino acid residue is located between the first labeling substance and the second labeling substance,
and wherein the peptide for temperature determination is cleaved at the at least one amino acid residue by heating whereby the first labeling substance is separated from the second labeling substance and the first labeling substance generates the optical change.

2. The method according to claim 1, wherein the sample is whole blood, serum, or plasma.

3. The method according to claim 1, wherein the peptide for temperature determination comprises an amino acid sequence selected from the group consisting of SEQ ID NOs: 16 to 32.

4. The method according to claim 1, wherein the optical change is a change in wavelength of an optical signal due to the peptide for temperature determination.

5. The method according to claim 4, wherein the change in wavelength of the optical signal is fluorescence generation.

6. The method according to claim 1, wherein
the first labeling substance is a fluorescent substance,
the second labeling substance is a quencher that quenches fluorescence from the fluorescent substance, and
the optical change is fluorescence generation.

7. The method according to claim 6, wherein the first labeling substance is 5-((2-aminoethyl)amino)naphthalene-1-sulfonic acid or 7-methoxycoumarin-4-acetic acid, and the second labeling substance is 4-[4-(dimethylamino)phenylazo]benzoic acid or 2,4-dinitrophenol.

8. The method according to claim 4, wherein
it is determined that the temperature of the mixture has reached the predetermined temperature when the intensity of the detected optical signal is higher than or equal to a predetermined threshold in the determining step, and
it is determined that the temperature of the mixture has not reached the predetermined temperature when the intensity of the detected optical signal is less than the predetermined threshold in the determining step.

* * * * *